US008153820B2

(12) United States Patent
Zierke et al.

(10) Patent No.: US 8,153,820 B2
(45) Date of Patent: Apr. 10, 2012

(54) METHOD FOR THE PRODUCTION OF N-SUBSTITUTED (3-DIHALOMETHYL-1-METHYLPYRAZOL-4-YL) CARBOXAMIDES

(75) Inventors: Thomas Zierke, Boehl-Iggelheim (DE); Joachim Rheinheimer, Ludwigshafen (DE); Michael Rack, Eppelheim (DE); Sebastian Peer Smidt, Mannheim (DE); Ansgar Gereon Altenhoff, Heidelberg (DE); Joachim Schmidt-Leithoff, Mannheim (DE); Nina Challand, Mannheim (DE)

(73) Assignee: BASF SE, Ludwigshafen (DE)

( * ) Notice: Subject to any disclaimer, the term of this patent is extended or adjusted under 35 U.S.C. 154(b) by 171 days.

(21) Appl. No.: 12/601,966

(22) PCT Filed: May 30, 2008

(86) PCT No.: PCT/EP2008/056712
§ 371 (c)(1),
(2), (4) Date: Nov. 25, 2009

(87) PCT Pub. No.: WO2008/145740
PCT Pub. Date: Dec. 4, 2008

(65) Prior Publication Data
US 2010/0174094 A1 Jul. 8, 2010

(30) Foreign Application Priority Data
Jun. 1, 2007 (EP) .................................... 07109463

(51) Int. Cl.
*C07D 231/10* (2006.01)
(52) U.S. Cl. .................................. 548/373.1; 548/374.1
(58) Field of Classification Search ................ 548/373.1, 548/374.1
See application file for complete search history.

(56) References Cited

U.S. PATENT DOCUMENTS

| 5,093,347 | A | 3/1992 | Graneto et al. |
| 2006/0262944 | A1 | 11/2006 | Rasmussen et al. |
| 2006/0276656 | A1 | 12/2006 | Lantzsch et al. |
| 2008/0015244 | A1 | 1/2008 | Dunkel et al. |
| 2010/0022782 | A1 | 1/2010 | Zierke et al. |
| 2010/0069646 | A1 | 3/2010 | Sukopp et al. |
| 2010/0174094 | A1 | 7/2010 | Zierke et al. |

FOREIGN PATENT DOCUMENTS

| DE | 39 34 924 | 4/1991 |
| DE | 103 31 496 | 1/2005 |
| JP | 59046273 | 3/1984 |
| WO | WO 92/12970 | 8/1992 |
| WO | WO 93/11117 | 6/1993 |
| WO | WO 03/070705 | 8/2003 |
| WO | WO 2005/042468 | 5/2005 |
| WO | WO 2005/044804 | 5/2005 |
| WO | WO 2007/031323 | 3/2007 |
| WO | WO 2007/051981 | * 5/2007 |
| WO | WO 2008/022777 | 2/2008 |
| WO | WO 2008/053043 | 5/2008 |
| WO | WO 2008/077907 | 7/2008 |
| WO | WO 2008/145740 | 12/2008 |
| WO | WO 2008/152138 | 12/2008 |

OTHER PUBLICATIONS

Huang, Zaifu. Studies on the synthesis of 3-substituted and 1,3-disubstituted pyrazoles via condensation of beta-chlorovinyl ketones with hydrazines. Gaodeng Xuexiao Huaxue Xuebao. 3(3) (1992) 367-373.*

(Continued)

*Primary Examiner* — Rebecca Anderson
*Assistant Examiner* — Samantha Shterengarts
(74) *Attorney, Agent, or Firm* — Brinks Hofer Gilson & Lione

(57) ABSTRACT

The present invention relates to a process for preparing N-substituted (3-dihalomethylpyrazol-4-yl)carboxamides of the formula (I)

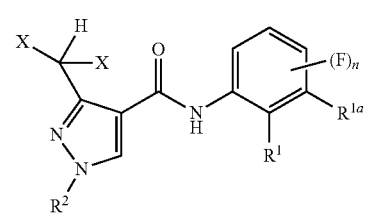

(I)

in which $R^1$ is optionally substituted phenyl or $C_3$-$C_7$-cycloalkyl, $R^{1a}$ is hydrogen or fluorine, or $R^{1a}$ together with $R^1$ is optionally substituted $C_3$-$C_5$-alkanediyl or $C_5$-$C_7$-cycloalkanediyl, $R^2$ is $C_1$-$C_6$-alkyl, $C_2$-$C_6$-alkenyl, $C_2$-$C_6$-alkynyl or $C_1$-$C_4$-alkoxy-$C_1$-$C_2$-alkyl, X is F or Cl and n is 0, 1, 2 or 3; which comprises
A) providing a compound of the formula (II)

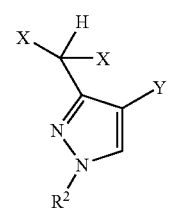

(II)

in which X is F or Cl, Y is Cl or Br and $R^2$ has one of the meanings given above and
B) reacting a compound of the formula (II) with carbon monoxide and a compound of the formula (III)

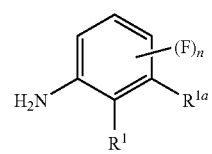

(III)

in which $R^1$, $R^{1a}$ and n have one of the meanings given above; in the presence of a palladium catalyst;
to intermediates used for the preparation according to the process according to the invention, and also to processes for their preparation.

29 Claims, No Drawings

OTHER PUBLICATIONS

International Search Report for International Application No. PCT/EP2008/056712.

International Preliminary Report on Patentability for International Application No. PCT/EP2008/056712.

Gupton, John T. et al., "The application of vinylogous iminium salt derivatives to the regiocontrolled preparation of heterocyclic appended pyrazoles", Tetrahedron, 2002, p. 5467-5474, vol. 58.

Merceron, Nathalie, et al., "C-Phosphanyl-C-chloroiminium salts as electrophilic carbene synthetic equivalents", Chemical Communications, 2002, p. 2250-2251.

Petrov, Viacheslav A. et al., "1,1,2,2-Tetrafluoroethyl-N,N-dimethylamine: a new selective fluorinating agent", Journal of Fluorine Chemistry, 2001, p. 25-31, vol. 109.

Brough, P.A., et al., "3-(5-chloro-2,4-dihydroxyphenyl)-Pyrazole-4-carboxamides as inhibitors of the Hsp90 molecular chaperone", Bioorganic & Medicinal Chemistry Letters, 2005, p. 5197-5201, vol. 15.

* cited by examiner

METHOD FOR THE PRODUCTION OF N-SUBSTITUTED (3-DIHALOMETHYL-1-METHYLPYRAZOL-4-YL) CARBOXAMIDES

This application is a National Stage application of International Application No. PCT/EP2008/056712 filed May 30, 2008, the entire contents of which is hereby incorporated herein by reference. This application also claims the benefit under 35 U.S.C. §119 of European Patent Application No. 07109463.5, filed Jun. 1, 2007, the entire contents of which is hereby incorporated herein by reference.

The present invention relates to a process for preparing N-substituted (3-dihalomethyl-pyrazol-4-yl)carboxamides, especially N-substituted (3-difluoromethylpyrazol-4-yl)-carboxamides, to intermediates used for the preparation and also to processes for their preparation.

WO 92/12970 describes (3-difluoromethyl-1-methylpyrazol-4-yl)carboxamides and their use as fungicides. They are prepared starting with a 4,4-difluoroacetoacetic ester which is reacted successively with trifluoroethyl orthoformate and with methylhydrazine, giving the (3-difluoromethyl-1-methylpyrazol-4-yl)carboxylate. This is then hydrolyzed to the carboxylic acid and, via the intermediate stage of the corresponding acid chloride, converted into the corresponding amide using a suitable amine.

WO 2005/044804 describes carboxylates of fluoromethyl-substituted heterocycles such as, inter alia, ethyl 3-difluoromethyl-1-methyl-1H-pyrazole-4-carboxylate, and also their preparation by halogen exchange on the corresponding carboxylates of chloromethyl-substituted heterocycles. Also described is the conversion of the resulting compounds into the corresponding carboxamides.

The unpublished EP 06123461.3 describes the preparation of (3-difluoromethyl-1-methylpyrazol-4-yl)carboxylates from 2-alkoxymethylene-4,4-trihaloacetoacetic esters by partial dehalogenation and reaction with a suitable hydrazine derivative. Also described is the conversion of the resulting compounds into the corresponding carboxamides.

Thus, the processes known from the prior art for preparing N-substituted (3-dihalo-methylpyrazol-4-yl)carboxamides all use the corresponding N-substituted (3-dihalo-methylpyrazol-4-yl)carboxylates as starting materials. However, the preparation of N-substituted (3-dihalomethylpyrazol-4-yl)carboxylates is comparatively complicated.

Accordingly, it is an object of the present invention to provide an alternative process for preparing N-substituted (3-dihalomethylpyrazol-4-yl)carboxamides which avoids the disadvantages of the prior art. In this process, the provision of the corresponding carboxylates, their hydrolysis and the subsequent conversion into the corresponding carboxamides should be replaced by a comparatively less complicated synthesis route.

Surprisingly, it has been found that this object is achieved by a synthesis in which the hitherto unknown N-substituted 4-bromo-3-dihalomethylpyrazoles of the formula (II) defined below are reacted with carbon monoxide and suitable anilines in the presence of a palladium catalyst. For their part, the compounds of the formula (II) can be obtained, for example, by halogenating corresponding compounds of the formula (IV) defined below.

Accordingly, the present invention provides a process for preparing compounds of the formula (I)

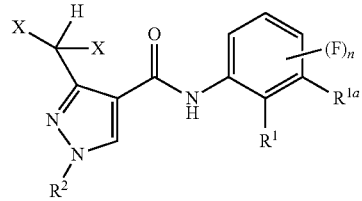

(I)

in which $R^1$ is phenyl or $C_5$-$C_7$-cycloalkyl which are unsubstituted or have 1, 2 or 3 substituents $R^{a1}$ independently of one another selected from the group consisting of halogen, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, $C_1$-$C_4$-haloalkylthio and $C_3$-$C_7$-cycloalkyl, $R^{1a}$ is hydrogen or fluorine, or $R^{1a}$ together with $R^1$, is $C_3$-$C_5$-alkanediyl or $C_5$-$C_7$-cycloalkanediyl, where $C_3$-$C_5$-alkanediyl and $C_5$-$C_7$-cycloalkanediyl are unsubstituted or have 1, 2 or 3 substituents selected from the group consisting of $C_1$-$C_4$-alkyl radicals, $R^2$ is hydrogen, $C_1$-$C_6$-alkyl, $C_2$-$C_6$-alkenyl, $C_2$-$C_6$-alkynyl or $C_1$-$C_4$-alkoxy-$C_1$-$C_2$-alkyl, X is F or Cl and n is 0, 1, 2 or 3;

which comprises

A) providing a compound of the formula (II)

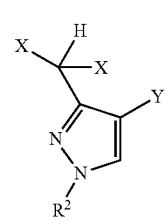

(II)

in which

X is F or Cl,

Y is Cl or Br and $R^2$ has one of the meanings given above; and

B) reacting a compound of the formula (II) with carbon monoxide and a compound of the formula (III),

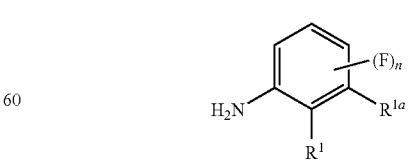

(III)

in which $R^1$, $R^{1a}$ and n have one of the meanings given above, in the presence of a palladium catalyst.

A specific subject-matter of the present invention relates to a process for preparing compounds of the formula (I.1)

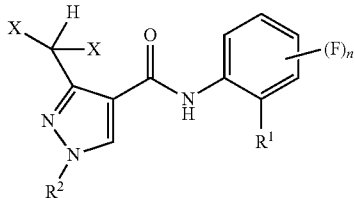

(I.1)

in which
R¹ is phenyl or $C_3$-$C_7$-cycloalkyl which are unsubstituted or have 1, 2 or 3 substituents $R^{a1}$ independently of one another selected from the group consisting of halogen, $C_1$-$C_8$-alkyl, $C_1$-$C_4$-alkoxy, $C_1$-$C_4$-alkylthio, $C_1$-$C_4$-haloalkyl, $C_1$-$C_4$-haloalkoxy, $C_1$-$C_4$-haloalkylthio and $C_3$-$C_7$-cycloalkyl,
R² is hydrogen, $C_1$-$C_6$-alkyl, $C_2$-$C_6$-alkenyl, $C_2$-$C_6$-alkynyl or $C_1$-$C_4$-alkoxy-$C_1$-$C_2$-alkyl,
X is F or Cl and
n is 0, 1, 2 or 3;
which comprises
A) providing a compound of the formula (II)

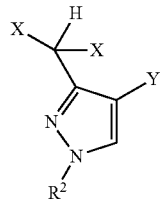

(II)

in which
X is F or Cl,
Y is Cl or Br and
R² has one of the meanings given above; and
B) reacting a compound of the formula (II) with carbon monoxide and a compound of the formula (III.1),

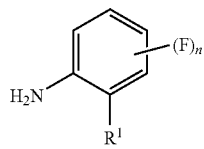

(III.1)

in which R¹ and n have one of the meanings given above, in the presence of a palladium catalyst,
i.e. a process according to the invention in which the compound of the formula (I) is selected from among compounds of the formula (I.1) in which R¹, R², X and n independently of one another have one of the meanings given for the components of the formula (I), and in which the compound of the formula (III) is selected from among compounds of the formula (III.1) in which R¹ and n independently of one another have one of the meanings given for the compounds of the formula (III).

The preferred embodiments described below for the compounds of the formulae (I) and (III) and their use apply correspondingly also to the compounds of the formulae (I.1) and (III.1) and their use.

The invention also provides the compounds of the formula (II), in particular compounds of the formula (II) in which X is fluorine.

The invention also provides their immediate precursor, compounds of the formula (IV)

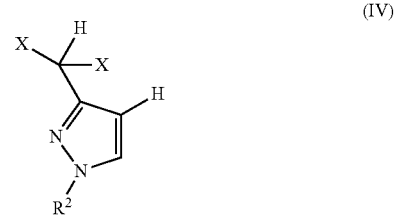

(IV)

in which R² has one of the meanings given above and X is chlorine or fluorine.

The invention furthermore provides the compounds of the formulae (VII), (VIII) and (IX),

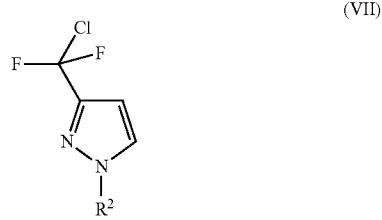

(VII)

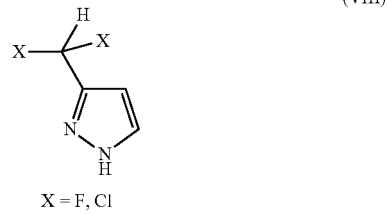

(VIII)

X = F, Cl

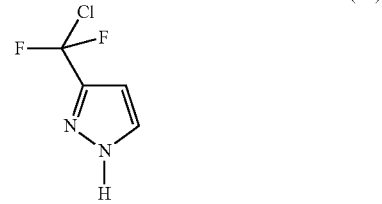

(IX)

which, as illustrated in more detail below, can be converted in a simple manner into the compounds of the formula (IV).

The invention furthermore provides processes for preparing the compounds of the formula (II) and also processes for preparing their synthesis precursors (IV), (VII), (VIII) and (IX).

The terms for organic groups used in the definition of the variables, such as, for example, the term "halogen", are collective terms which represent the individual members of these groups of organic moieties. In each case, the prefix $C_x$-$C_y$ denotes the number of possible carbon atoms.

The term "halogen" refers in each case to fluorine, chlorine, bromine or iodine, especially fluorine or chlorine.

Examples of other meanings are:

The term "alkyl", as used in $C_1$-$C_8$-alkyl and in the terms $C_1$-$C_4$-alkoxy, $C_1$-$C_4$-alkoxy-$C_1$-$C_2$-alkyl and $C_1$-$C_4$-alkylthio, refers to a saturated straight-chain or branched hydrocarbon group comprising especially 1 to 8 carbon atoms or 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethylpentyl, 2-ethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1-ethyl-1-methylbutyl, 1-ethyl-2-methylbutyl, 1-ethyl-3-methylbutyl, octyl, 1-methylheptyl, 2-methylheptyl, 3-methylheptyl, 4-methylheptyl, 5-methylheptyl, 6-methylheptyl and their isomers. $C_1$-$C_4$-alkyl comprises, for example, methyl, ethyl, propyl, 1-methylethyl, butyl, 1-methylpropyl, 2-methylpropyl or 1,1-dimethylethyl.

The term "$C_2$-$C_6$-alkenyl" refers to monounsaturated straight-chain or branched hydrocarbon radicals having 2 to 6 carbon atoms, preferably 2 to 4 carbon atoms, and a C—C double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

The term "$C_2$-$C_6$-alkynyl" refers to monounsaturated straight-chain or branched hydrocarbon radicals having 2 to 6 carbon atoms, preferably 2 to 4 carbon atoms, and a C—C triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, dimethyl-3-butynyl, 3,3-dimethyl-1-butynyl, 3,3-dimethyl-2-butynyl, ethyl-2-butynyl, 1-ethyl-3-butynyl, 2-ethyl-3-butynyl or 1-ethyl-1-methyl-2-propynyl.

The term "$C_1$-$C_4$-alkoxy" refers to straight-chain or branched saturated alkyl groups comprising 1 to 4 carbon atoms, which groups are attached via an oxygen atom. Examples include $C_1$-$C_4$-alkoxy, such as, for example, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$ and $OC(CH_3)_3$.

The term "$C_1$-$C_4$-alkylthio" refers to straight-chain or branched saturated alkyl groups comprising 1 to 4 carbon atoms, which groups are attached via a sulfur atom. Examples include $C_1$-$C_4$-alkylthio, such as, for example, methylthio, ethylthio, $SCH_2$—$C_2H_5$, $SCH(CH_3)_2$, n-butylthio, $SCH(CH_3)$—$C_2H_5$, $SCH_2$—$CH(CH_3)_2$ and $SC(CH_3)_3$.

The term "$C_1$-$C_4$-haloalkyl", as used herein and in the haloalkyl moieties of $C_1$-$C_4$-halo-alkoxy and $C_1$-$C_4$-haloalkylthio, refers to straight-chain or branched alkyl groups having 1 to 4 carbon atoms, where some or all of the hydrogen atoms of these groups are replaced by halogen atoms, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, etc.

The term "$C_1$-$C_4$-haloalkoxy" refers to $C_1$-$C_4$-haloalkyl groups, as defined above, which are attached via an oxygen atom. Examples include mono-, di- and trifluoromethoxy, mono-, di- and trichloromethoxy, 1-fluoroethoxy, 1-chloroethoxy, 2-fluoroethoxy, 2-chloroethoxy, 1,1-difluoroethoxy, 1,1-dichloroethoxy, 1,2-difluoroethoxy, 1,2-dichloroethoxy, 2,2-difluoroethoxy, 2,2-dichloroethoxy, 2,2,2-trifluoroethoxy, 1,1,2,2-tetrafluoroethoxy, 2,2,2-trichloroethoxy, 1,1,1,2,3,3-hexafluoroisopropoxy, 1,1,2,3,3,3-hexafluoroisopropoxy, 2-chloro-1,1,2-trifluoroethoxy or heptafluoroisopropoxy.

The term "$C_1$-$C_4$-haloalkylthio" refers to $C_1$-$C_4$-haloalkyl groups, as defined above, which are attached via a sulfur atom. Examples include mono-, di- and trifluoro-methylthio, mono- di- and trichloromethylthio, 1-fluoroethylthio, 1-chloroethylthio, 2-fluoroethylthio, 2-chloroethylthio, 1,1-difluoroethylthio, 1,1-dichloroethylthio, 1,2-difluoroethylthio, 1,2-dichloroethylthio, 2,2-difluoroethylthio, 2,2-dichloroethylthio, 2,2,2-trifluoroethylthio, 1,1,2,2-tetrafluoroethylthio, 2,2,2-trichloroethylthio, 1,1,1,2,3,3-hexafluoroisopropylthio, 1,1,2,3,3,3-hexafluoroisopropylthio, 2-chloro-1,1,2-trifluoro-ethylthio or heptafluoroisopropylthio.

The term "$C_3$-$C_7$-cycloalkyl", as used herein, describes cyclic hydrocarbon radicals comprising 3 to 7 carbon atoms. Examples of cyclic radicals are cyclopropyl, cyclobutyl, cyclopentyl, cyclohexyl or cycloheptyl.

The term "alkanediyl", as used in $C_3$-$C_5$-alkanediyl, refers to saturated straight-chain hydrocarbon groups comprising 3 to 5 carbon atoms which are attached via the two terminal carbon atoms, such as propane-1,3-diyl, butane-1,4-diyland pentane-1,5-diyl.

The term "cycloalkanediyl", as used in $C_5$-$C_7$-alkanediyl, refers to saturated cyclic hydrocarbon groups comprising 5 to 7 carbon atoms as ring members, which groups are attached via any two carbon atoms, such as cyclopentane-1,3-diyl, cyclohexane-1,3-diyl, cyclohexane-1,4-diyl, cycloheptane-1,3-diyl and cycloheptane-1,4-diyl.

In the process according to the invention for preparing compounds of the formula (I) from compounds of the formulae (II) and (III), in step B the compounds of the formulae (II) and (III) are preferably employed in a molar ratio (II):(III) of from 0.5:1 to 2:1, preferably from 0.8:1 to 1.2:1. In particular, the compound of the formula (III) is employed in a slight excess, based on the compound (II), i.e. the molar ratio (II):(III) is <1, for example in the range of from 0.5:1 to <1:1, in particular in the range of from 0.8:1 to 0.95:1.

Suitable palladium catalysts for the reaction of the compounds of the formula (II) with compounds of the formula (III) are palladium-containing compounds in which the palladium has an oxidation state of 0 or 2.

Examples of palladium-containing compounds having an oxidation state of 0 are palladium(0) ligand complexes, such as palladium(0)tetrakis(triphenylphosphine), palladium(0) tetrakis(diphenylmethylphosphine) or palladium(0)-bis (DIPHOS), or metallic palladium which may be supported, if appropriate. Metallic palladium is preferably applied to an inert support, such as activated carbon, alumina, barium sulfate, barium carbonate or calcium carbonate. The reaction in the presence of metallic palladium is preferably carried out in the presence of suitable complex ligands.

Examples of palladium-containing compounds having an oxidation state of 2 are palladium(II) ligand complexes, such as palladium(II) acetylacetonate, or compounds of the formula $PdX_2L_2$ in which X is halogen and L is a monovalent ligand, in particular a ligand of the formula (A) or (B) shown below, and also palladium(II) salts, such as, for example, palladium acetate or palladium chloride, preferably palladium chloride.

If palladium(II) salts are used, the reaction is preferably carried out in the presence of suitable complex ligands, especially in the complex ligands of the formulae (A) and (B) shown below.

The palladium catalyst may be employed in the form of a finished palladium complex or as a palladium compound which, under the reaction conditions, forms, as a pre-catalyst, the catalytically active compound together with suitable ligands.

Suitable complex ligands for the reaction according to the invention of compounds of the formula (II) with compounds of the formula (III) are, for example, mono- or bidentate phosphines of the formulae (A) and (B) shown below

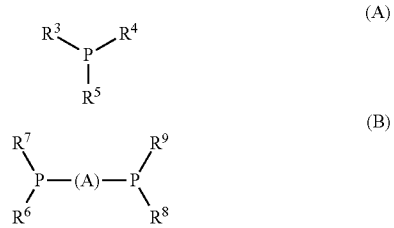

in which $R^3$ to $R^9$ independently of one another are $C_1$-$C_6$-alkyl, $C_5$-$C_8$-cycloalkyl, adamantyl, aryl-$C_1$-$C_2$-alkyl or, preferably, ferrocenyl or aryl which may optionally be substituted by $C_1$-$C_4$-alkyl or $C_1$-$C_4$-alkoxy, and A is a straight-chain bivalent hydrocarbon group having preferably 2 to 5 carbon atoms which is unsubstituted or optionally substituted, where the bivalent hydrocarbon group may be part of a mono- or bicyclic ring which for its part is unsubstituted or may have further substituents.

A in the compounds of the formulae (A) and (B) is especially $C_2$-$C_4$-alkylene, $C_0$-$C_1$-alkyleneferrocenyl, 1,1'-biphenyl-2,2'-diyl or 1,1'-binaphthyl-2,2'-diyl, where the four last-mentioned groups may optionally be substituted by $C_1$-$C_4$-alkyl or $C_1$-$C_4$-alkoxy and where $C_1$-$C_4$-alkylene may additionally have one or more substituents selected from the group consisting of $C_3$-$C_7$-cycloalkyl, aryl and benzyl. In this context, aryl is naphthyl or optionally substituted phenyl. Aryl is preferably phenyl or tolyl, particularly preferably phenyl. $C_0$-$C_1$-Alkyleneferrocenyl is especially ferrocenediyl, where the two phosphorus atoms are in each case attached to one cyclopentadiene of the ferrocene, or is methyleneferrocenyl, where one of the phosphorus atoms is attached via the methylene group to a cyclopentadiene, the second phosphorus atom is attached to the same cyclopentadiene and the methylene group may optionally have 1 or 2 further substituents selected from $C_1$-$C_4$-alkyl.

The complex ligands used in the process according to the invention for reacting compounds of the formula (II) with compounds of the formula (III) are preferably bidentate phosphines, such as 1,3-bis(diphenylphosphino)propane (DPPP), 1,3-bis(diphenylphosphino)ethane, 1,3-bis(dicyclohexylphosphino)propane (DCPP), ferrocenyl-containing phosphines of the JosiPhos type, 1,1'-bis(diphenylphosphino)-ferrocene (DPPF) or 2,2-dimethyl-1,3-bis(diphenylphosphino) propane and particularly preferably 2,2-dimethyl-1,3-bis (diphenylphosphino)propane.

In the process according to the invention, the palladium catalyst is preferably employed in an amount of from 0.01 to 5 mol %, particularly preferably from 0.1 to 1 mol %, based on the amount of the pyrazole of the formula (II) used.

In a preferred embodiment, the process according to the invention for reacting compounds of the formula (II) with compounds of the formula (III) is carried out in the presence of an auxiliary base.

Suitable auxiliary bases are, for example, basic alkali metal salts and tertiary amines.

Examples of basic alkali metal salts are potassium phosphate, sodium phosphate, potassium carbonate, sodium carbonate, potassium acetate or sodium acetate. Preferably, the alkali metal salt should be essentially water-free. Particular preference is given to using dry potassium carbonate or potassium phosphate. In this embodiment, alkali metal salts are preferably employed in an amount of at least one, particularly preferably 1 to 4 and especially about 2 molar equivalents, based on the amount of the pyrazole compound of the formula (II) used.

Suitable tertiary amines are, for example, tri($C_1$-$C_6$-alkyl) amines, such as trimethylamine, triethylamine or diisopropylethylamine, N-methylpiperidine, pyridine, substituted pyridines, such as 2,4,6-trimethylpyridine (collidine), 2,6-dimethylpyridine (lutidine), 2-methylpyridine, (α-picoline), 3-methylpyridine (β-picoline), 4-methylpyridine (γ-picoline) and 4-dimethylaminopyridine, and also bicyclic amines, such as 1,4-diaza-bicyclo[2.2.2]octane, 1,8-diazabicyclo[5.4.0] undec-7-ene or 1,5-diazabicyclo[4.3.0]non-5-ene. Particular preference is given to using triethylamine, pyridine or 1,8-diaza-bicyclo[5.4.0]undec-7-ene. Tertiary amines may be employed in an amount of from 0.1 to 4 molar equivalents, based on the amount of the pyrazole compound of the formula (II) used.

In a preferred embodiment of the process according to the invention, the reaction of a compound of the formula (II) with a compound of the formula (III) is carried out in the presence of at least one tertiary amine and at least one alkali metal salt.

In this embodiment, the alkali metal salt is preferably employed in an amount of from 1 to 4 and especially about 2 molar equivalents, based on the amount of the pyrazole compound of the formula (II) used. In this embodiment, the tertiary amine is preferably employed in an amount of from 0.1 to 4, preferably from 0.2 to 0.7, molar equivalents, based on the amount of the pyrazole compound of the formula (II) used.

In this embodiment, the auxiliary base is preferably employed in a total amount of from 2 to 5 molar equivalents, based on the amount of the pyrazole compound of the formula (II) used.

The reaction of the compound of the formula (II) with a compound of the formula (III) is preferably carried out in an organic solvent. Suitable solvents for the reaction of compounds of the formula (II) with compounds of the formula (III) are polar solvents, for example amides, such as dimethylformamide, dimethylacetamide, or N-methyl-pyrrolidone, ureas, such as 1,3-dimethyl-2-imidazolidinone (DMEU) or 1,4-dimethyl-hexahydro-2-pyrimidinone (DMPU), ethers, such as tetrahydrofuran (THF) and 1,4-dioxane, sulfolane, dimethyl sulfoxide (DMSO) or nitriles, such as acetonitrile or propionitrile, and also mixtures of these solvents. Preference is given to using nitriles such as, in particular, acetonitrile. The solvent used is preferably essentially water-free, i.e. the solvent has a water content of less than 1000 ppm and in particular not more than 100 ppm.

The reaction of compounds of the formula (II) with compounds of the formula (III) in the process according to the invention is preferably carried out at a temperature of from 100 to 150, particularly preferably at a temperature of from 110 to 130.

In the reaction of compounds of the formula (II) with compounds of the formula (III), the CO partial pressure is preferably in a range of from 0.9 to 100 bar, particularly preferably in a range of from 2 to 20 bar and especially in a range of from 5 to 10 bar.

The reaction mixtures obtained in the reaction of compounds of the formula (II) with compounds of the formula (III) are generally subjected to aqueous work-up, i.e. the reaction mixture obtained is brought into contact with water or an aqueous solution. After acidification of the water-containing reaction mixtures obtained in this manner, the compounds of the formula (I) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

In a preferred embodiment of the process according to the invention, a compound of the formula (II) in which $R^2$ is $C_1$-$C_6$-alkyl, $C_2$-$C_6$-alkenyl, $C_2$-$C_6$-alkynyl or $C_1$-$C_4$-alkoxy-$C_1$-$C_2$-alkyl is reacted under the conditions mentioned above with a compound of the formula (III) to give a compound of the formula (I).

In a further preferred embodiment of the process according to the invention, a compound of the formula (II) in which Y is Br is reacted under the conditions mentioned above with a compound of the formula (III) to give a compound of the formula (I).

The process according to the invention is suitable especially for preparing compounds of the formulae (I.a), (I.b) and (I.c).

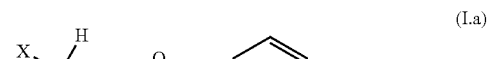

(I.a)

(I.b)

(I.c)

The process according to the invention is likewise suitable for preparing compounds of the formulae (I.e).

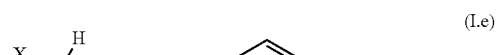

(I.e)

The present invention preferably provides processes for preparing compounds of the general formula (I) or (I.a), (I.b) and (I.c) or (I.e) in which X is fluorine.

The compounds of the formula (II) employed for preparing compounds (I) can be prepared, for example, using the methods below.

In a first preferred embodiment, provision of a compound of the formula (II) in which Y is Br or Cl comprises, A.1) providing a compound of the formula (IV)

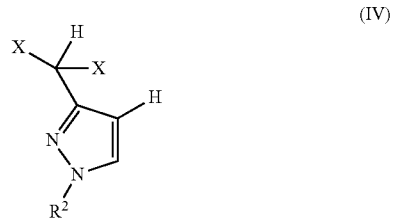

in which
X represents chlorine or fluorine and
$R^2$ has one of the meanings given above, A.2) if appropriate, in the case that X in the compound of the formula (IV) is chlorine, a halogen exchange for fluorine and A.3) chlorinating or brominating a compound of the formula (IV).

The bromination of the compounds of the formula (IV) with bromine ($Br_2$) is preferably carried out in an inert solvent, for example in a halogenated hydrocarbon, such as dichloromethane. Here, the reaction temperature is preferably in the range of from −5 to 50° C. and in particular at room temperature. Further reaction conditions which achieve the same purpose are known to the person skilled in the art.

The bromination of compounds of the formula (IV) can also preferably be carried out with N-bromosuccinimide (NBS) or 1,3-dibromo-5,5-dimethylhydantoin (DDH) and especially with NBS. The chlorination of compounds of the formula (IV) is preferably using N-chlorosuccinimide (NCS). Solvents suitable for this purpose are in particular polar solvents, such as dimethylformamide, N-methylpyrrolidinone, 1,3-dimethyl-2-imidazolidinone, dimethylacetamide, dimethylethyleneurea, dimethylpropyleneurea (DMPU) or tetramethylurea, or mixtures of these solvents. The reaction temperature is usually in the range of from −10 to 30° C.

The chlorination or bromination is preferably carried out using a compound of the formula (IV) in which X is fluorine.

Surprisingly, it has now been found that the compounds of the formula (IV), the preparation of which frequently yields mixtures with the respective isomers of the formula (Iso-IV) difficult to separate,

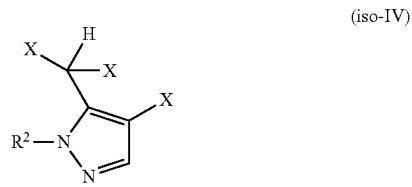

are more reactive to chlorination or bromination than the corresponding compounds of the formula (Iso-IV). In the formula (Iso-IV), X and $R^2$ have the meaning given for formula (IV). Owing to the differences in reactivity, it is possible to chlorinate or brominate selectively the desired isomer in mixtures of the compounds of the formulae (IV) and (iso-IV), giving a mixture of the compounds (II) and (iso-IV) which is much easier to separate than the mixture of the compounds (IV) and (iso-IV).

Accordingly, in a specific embodiment of the process according to the invention, the compound of the formula (IV) is provided in the form of a mixture with the corresponding 5-isomer of the formula (Iso-IV), and, after chlorination or bromination of the compound of the formula (IV), the compound of the formula (II) is separated from the unreacted compound of the formula (Iso-IV). Suitable separation methods are, for example, fractional distillation or rectification. By adopting this procedure, it is possible, in an advantageous manner, to avoid high yield losses when separating the compound of the formula (IV) from the compounds of the formula (Iso-IV). Here, it has been found to be advantageous to carry out the bromination of the compounds of the formula (IV) using bromine ($Br_2$) or NBS and to carry out the chlorination using NCS, as described above. The procedure described is particularly suitable for separating mixtures in which X is fluorine.

In the context of the present invention, the conversion of a dichloromethyl-substituted compound into the corresponding difluoromethyl-substituted compound in the presence of a fluorinating agent is referred to as halogen exchange. Suitable fluorinating agents are, in principle, all fluorinating agents customarily used for halogen exchange reactions. In this embodiment, the halogen exchange is preferably carried out by reaction with a fluorinating agent selected from the group consisting of alkali metal fluorides, cobalt(III) fluoride, antimony fluoride, molybdenum fluoride, hydrogen fluoride, hydrogen fluoride/pyridine mixtures, tertiary ammonium hydrofluorides and trialkylamine hydrofluorides of the general formula $n*HF/N(C_1-C_4\text{-alkyl})_3$, where n is 1, 2 or 3. Particularly preferably, the halogen exchange is carried out by reaction with trialkylamine hydrofluorides, such as triethylamine trishydrofluoride, tri-n-butylamine trishydrofluoride, and very particularly preferably with triethylamine trishydrofluoride.

The fluorinating agent is usually employed in a molar ratio of fluoride equivalents per chlorine atom to be replaced in the range of from 1:1 to 3:1. Preferably, the fluorinating agent is employed in a molar ratio in the range of from 1:1 to 1.5:1.

The halogen exchange reaction is preferably carried out at a temperature in the range of from 70 to 180° C., in particular at a temperature in the range of from 80 to 160° C.

The halogen exchange reaction can be carried out at atmospheric pressure or in an autoclave under autogenous pressure. Preferably, the pressure is in a range of from 0.1 to 50 bar, especially in the range of from 1 to 10 bar.

The halogen exchange reaction according to the invention can, if appropriate, be carried out in the presence of a diluent. For this purpose, preference is given to using nitriles, such as acetonitrile, halogenated hydrocarbons, such as chlorobenzene, dichlorobenzene, dichloromethane, chloroform, carbon tetrachloride, dichloroethane, trifluorochloromethane, 1,1,2-trifluoro-1,2,2-trichloroethane or trichloroethane, hydrocarbons, such as petroleum ether, hexane, heptane, cyclohexane, methylcyclohexane, benzene, toluene, xylene or decalin, ethers, such as diisopropyl ether, methyl tert-butyl ether, methyl tert-amyl ether, dioxane, tetrahydrofuran, 1,2-dimethoxyethane, 1,2-diethoxyethane or anisole, or diethyl glycol.

The compounds of the formula (IV) are novel and suitable for use as intermediates of compounds of the formula (II) and consequently also of compounds of the formula (I). Accordingly, the present invention also provides compounds of the formula (IV). From among these, preference is given to compounds of the general formula (IV) in which X is fluorine. However, the present invention also provides compounds of the formula (IV) in which X is chlorine.

Suitable methods for providing compounds of the formula (IV) are, for example, the processes shown below.

In a first embodiment according to the invention. the provision of a compound of the formula (IV) comprises the following steps:

A.1.1a) providing a compound of the formula (V)

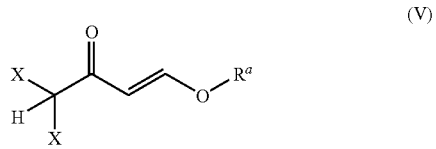

in which
$R^a$ $C_1$-$C_6$-alkyl or $C_1$-$C_6$-alkenyl and
X is Cl or fluorine and A.1.2a) reacting a compound of the formula (V) with a hydrazine compound of the formula $R^2HN$—$NH_2$ in which $R^2$ has one of the meanings given above.

The provision of a compound of the formula (V) in which X is chlorine by reaction of dichloroacetyl chloride with ethyl vinyl ether is known in principle (Effenberg, Chem. Ber. 1982, 115, 2766). Depending on the reaction conditions, this reaction gives rise to a large number of byproducts. In the context of the present invention, the reaction conditions mentioned below have been found to be particularly suitable. Dichloroacetyl chloride is reacted with ethyl vinyl ether under reflux conditions, i.e. at a temperature of about 38° C. at atmospheric pressure. Alternatively, the reaction can also be carried out with initial cooling, i.e. preferably at from −5 to 10° C., and then be brought to completion at a higher temperature. It is also possible to provide compounds of the formula (V) from other alkyl vinyl ethers.

The alkyl vinyl ether is employed in excess, i.e. preferably in an amount of from 3 to 15 and particularly preferably in an amount of from 6 to 10 molar equivalents, based on the amount of dichloroacetyl chloride to be reacted. After the reaction has ended, excess alkyl vinyl ether is removed by distillation. If required, the alkyl vinyl ether is removed after addition of an inert solvent with a relatively high boiling point, such as toluene, by coevaporation. If necessary, the compound of the formula (V) which remains as a residue can be purified by distillation. In a special embodiment, the further reaction with methylhydrazine is carried out without prior isolation of the compound of the formula (V).

Compounds of the formula (V) in which X is fluorine can be prepared analogously by reacting difluoroacetyl chloride with ethyl vinyl ether.

For the subsequent reaction of a compound of the formula (V) with a hydrazine compound of the formula $R^2HN$—$NH_2$ in which $R^2$ has one of the meanings given above and is preferably methyl, it has been found to be advantageous in particular with respect to the regioselectivity of the formation of compounds of the formula (IV) over the corresponding 5-dihalomethyl-substituted isomers to use aromatic hydrocarbons, such as benzene, toluene, ethylbenzene, xylenes, cumene, chlorobenzene, nitrobenzene or tert-butylbenzene, or a mixture of these solvents with water, as solvent. The reaction can be carried out in the absence of water, i.e. the concentration of water, based on the total amount of solvent, is less than 0.5% by volume. Alternatively, the reaction can be carried out in the presence of water. Preferably, the amount of water does not exceed 30% by volume, in particular 15% by volume, based on the total amount of organic solvent+water, and is preferably in the range of from 0.5 to 30% by volume, in particular in the range of from 1 to 15% by volume, based on the total amount of organic solvent+water.

The reaction of a compound of the formula (V) with a hydrazine compound of the formula $R^2HN$—$NH_2$ in which $R^2$ has one of the meanings given above is preferably carried out at temperatures of from 60 to 150° C. In general, the upper temperature limit is the boiling point of the solvent in question when the reaction is carried out under atmospheric pressure.

The hydrazine compound of the formula $R^2HN$—$NH_2$ is preferably employed in at least equimolar amounts or in excess. Preferably, from 1.0 to 1.2 mol, in particular from about 1.01 to 1.1 mol, of the hydrazine compound of the formula $R^2HN$—$NH_2$, in particular methylhydrazine, are employed per mole of the compound (V).

In the reaction of the compound (V) with methylhydrazine, the hydrazine compound of the formula $R^2HN$—$NH^2$ is generally added, preferably as a solution in the organic solvent to be used for the reaction or in water, to the compound of the formula (V) or to a solution thereof in an organic solvent or solvent/water mixture. Addition in reverse order or simultaneous addition of the starting materials is also possible.

In a special embodiment according to the invention, the volatile components formed during the reaction of the compound (V) with a hydrazine compound of the formula $R^2HN$—$NH_2$ are removed continuously from the reaction mixture by distillation. The solvent which is possibly simultaneously removed from the reaction mixture is replaced continuously by the same amount of fresh solvent.

In an alternative embodiment according to the invention, the compound of the formula (IV) are provided from compounds of the formula (V) by reaction of a compound of the formula (V) with hydrazine to give a compound of the formula (VIII)

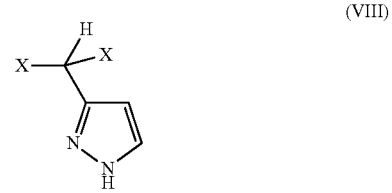

in which X is Cl or fluorine, and subsequent N-alkylation of the compound of the formula (VIII).

In this embodiment, hydrazine is preferably employed in the form of hydrazine hydrate.

Hydrazine, if appropriate as hydrazine hydrate, is preferably employed in at least equimolar amounts or in excess. Preferably, from 1.0 to 2.0 mol, in particular from about 1.2 to 1.8 mol, of hydrazine are employed per mole of the compound of the formula (V) to be reacted.

The reaction of compounds of the formula (V) with hydrazine is generally carried out by adding the compound of the formula (V), preferably in the form of a solution in a suitable organic solvent, to the hydrazine compound, preferably to a solution of hydrazine hydrate. Preferably, hydrazine is initially charged as a solution in an organic solvent or solvent/water mixture. Alternatively, hydrazine, especially hydrazine hydrate, preferably as a solution in an organic solvent or solvent/water mixture, may also be added to the compound of the formula (V) or to a solution thereof in an organic solvent or solvent/water mixture.

Organic solvents suitable for the reaction with hydrazine, especially hydrazine hydrate, are protic polar solvents, for example aliphatic alcohols having preferably 1 to 4 carbon atoms, such as methanol, ethanol, n-propanol, isopropanol, n-butanol, isobutanol or tert-butanol, or carboxylic acids, such as acetic acid, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethyl-urea, or aliphatic nitriles, such as acetonitrile or propionitrile, and also mixtures of the solvents mentioned above.

The reaction is preferably carried out in a protic polar solvent, in particular in a $C_1$-$C_4$-alcohol or a carboxylic acid and particularly preferably in methanol, ethanol, acetonitrile or acetic acid, or in a mixture of a protic polar solvent with an aprotic polar solvent or in a mixture of these solvents with water. The reaction can be carried out in a water-free manner, i.e. the concentration of water, based on the total amount of solvent, is less than 0.5% by volume. However, the reaction in step b) is preferably carried out in the presence of water. The amount of water does preferably not exceed 30% by volume, in particular 15% by volume, based on the total amount of organic solvent+water, and is preferably in the range of from 0.5 to 30% by volume, in particular in the range of from 1 to 15% by volume, based on the total amount of organic solvent+water.

The reaction is preferably carried out at temperatures of from −80 to −100° C. In general, the upper temperature limit is the boiling point of the solvent in question when the reaction is carried out at atmospheric pressure. Preferably, a reaction temperature of 60° C. and in particular 40° C. is not exceeded. Frequently, for practical reasons, the reaction is carried out at room temperature.

Work-up of the reaction mixture and isolation of the pyrazole compound of the formula (VIII) are carried out in a customary manner, for example by removing the solvent, for example by distillation or by aqueous extractive work-up or by a combination of these measures. Further purification can be carried out, for example, by crystallization or by chromatography. However, frequently, the product is already obtained in a purity which does not require further purification steps.

The compounds of the formula (VIII) are then converted by N-alkylation into compounds of the formula (IV).

Suitable conditions for the N-alkylation of pyrazoles are known per se. For the N-alkylation of compounds of the formula (VIII), the use of alkylating agents in the presence of inorganic bases has been found to be particularly suitable.

Suitable alkylating agents are, for example, compounds of the formula LG-$R^2$. In the alkylating agents LG-$R^2$, LG can be selected from the group consisting of halogen and O—$SO_2$—$R^m$, in which $R^m$ is $C_1$-$C_4$-alkyl, $C_1$-$C_4$-alkoxy or aryl which are optionally substituted by halogen, $C_1$-$C_4$-alkyl or halo-$C_1$-$C_4$-alkyl. Here, $R^2$ has one of the meanings given above and is in particular $C_1$-$C_6$-alkyl and especially methyl.

The alkylation is usually carried out at temperatures in the range of from −78° C. to the boiling point of the reaction mixture, preferably at from −50° C. to 65° C., especially preferably at from −30° C. to 65° C. In general, the reaction is carried out in a solvent, preferably in an inert organic solvent.

Suitable solvents are inter alia toluene, dichloromethane, tetrahydrofuran or dimethylformamide, or mixtures thereof.

Suitable bases are inorganic compounds, such as alkali metal and alkaline earth metal hydroxides, such as lithium hydroxide, sodium hydroxide, potassium hydroxide or calcium hydroxide, alkali metal or alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate, cesium carbonate and calcium carbonate, and also alkali metal bicarbonates, such as sodium bicarbonate. Particular preference is given to alkali metal and alkaline earth metal carbonates or alkali metal and alkaline earth metal hydroxides. It is, of course, also possible to use mixtures of different bases.

The bases are generally employed in equimolar amounts. However, they can also be used in excess or, for their part, as a solvent. In a preferred embodiment of the process according to the invention, the base is added in an equimolar amount or in an essentially equimolar amount.

In a further preferred embodiment of the process according to the invention, the N-alkylation is an N-methylation. In this embodiment, particularly suitable alkylating agents are dimethyl sulfate and trimethylphosphate.

The alternative path illustrated above is especially preferred when X in the compounds of the formula (V) is fluorine; in contrast, the reaction, described above, of compounds of the formula (V) with hydrazine compounds of the formula $R^2$HN—$NH_2$ is especially preferred when X is chlorine.

Alternatively, compounds of the formula (IV) in which X is chlorine can also be prepared by reacting 1,1,4-trichloro-3-buten-2-one with 1,1-dimethylhydrazine.

Compounds of the formula (IV) in which X is chlorine can be converted as shown above by halogen exchange into compounds of the formula (IV) in which X is fluorine.

Alternatively, compounds of the formula (VIII) in which X is Cl can be subjected to a halogen exchange and a subsequent N-alkylation, which gives a compound of the formula (IV) in which X is fluorine.

In a further embodiment according to the invention, the provision of a compound of the formula (IV) comprises the following steps:

A.1.1b) providing a compound of the formula (VI),

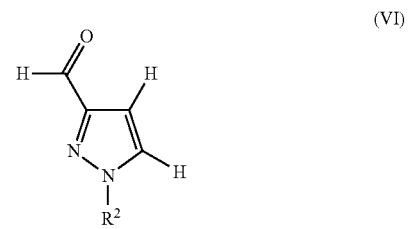

(VI)

in which $R^2$ has one of the meanings given above; and also

A.1.2b) reacting a compound of the formula (VI) by converting the carbonyl group into a dihalomethyl group using a suitable halogenating agent.

The provision of a compound of the formula (VI) and the conversion of a carbonyl group into a dihalomethyl group is preferably carried out under the conditions described above, or analogously to the methods described above for the 4-chlorinated or 4-brominated compounds of the formula (VI).

In a further embodiment according to the invention, the provision of a compound of the formula (IV) comprises the following steps:

A.1.1c) deprotonating a propargylaldehyde acetal,
A.1.2c) reacting the deprotonated propargylaldehyde acetal from step A.1.1 c) with a compound of the formula CHX₂Cl in which X is F or Cl, and
A.1.3c) subsequently converting the reaction product from step A.1.2c) into a compound of the formula (IV) using a hydrazine compound of the formula $R^2HN-NH_2$ in which $R^2$ has one of the meanings given above.

Propargylaldehyde acetals, in particular propargylaldehyde dimethyl acetal, can be obtained, for example, by acetalization of acrolein with trialkyl formates, for example trimethyl formate, subsequent addition of bromine and double elimination of HBr (Tetrahedron 2001, 56 (3), 425).

The deprotonation of the propargylaldehyde acetal is preferably carried out by reaction with a suitable base. Suitable bases are, for example, alkyllithium compounds, such as butyllithium, or alkali metal amides, such as $LiNH_2$ or $NaNH_2$.

The deprotonation is usually carried out in a suitable dry solvent at a temperature of from −120 to −20° C., preferably from −100 to −50° C. Dry solvent means that the solvent has a water content of less than 1000 ppm and in particular not more than 100 ppm. Examples of suitable solvents are, for example, cyclic or acyclic ethers, such as diethyl ether, tert-butyl methyl ether (MTBE), diisopropyl ether, tetrahydrofuran (THF) or dioxane, aromatic or (cyclo)aliphatic hydrocarbons, such as toluene, xylenes, hexane, cyclohexane and the like, and also mixtures of these solvents.

The reaction of the deprotonated propargylaldehyde acetal is expediently carried out without prior isolation of the deprotonated compound, under the conditions described above by adding a compound of the formula $CHX_2Cl$. The compound $CHX_2Cl$ is frequently added in the form of a solution, preferably as a solution in the solvent used for the reaction. If X in the compound of the formula $CHX_2Cl$ is F, the compound is preferably added as a gas.

Usually, the dihalomethyl-substituted propargylaldehyde dialkyl acetal obtained in this manner is isolated by aqueous extractive work-up. Further purification of the reaction product can be carried out, for example, by distillation.

The conversion of the dihalomethyl-substituted propargylaldehyde dialkyl acetal into a compound of the formula (IV) using a hydrazine compound of the formula $R^2HN-NH_2$, especially methylhydrazine, is preferably carried out in the presence of concentrated sulfuric acid. Here, the sulfuric acid is employed in about equimolar amounts. Preferably, in this special embodiment the reaction is carried out at temperatures of from 60 to 150° C. In general, when the reaction is carried out at atmospheric pressure, the upper temperature limit is the boiling point of the solvent used. A preferred solvent for this special embodiment is acetic acid (glacial acetic acid). In this special embodiment, the hydrazine compound of the formula $R^2HN-NH_2$ is preferably employed in excess. Preferably, from 1 to 3 mol, in particular from about 1.5 to 2.5 mol, of the hydrazine compound are employed per mole of the dihalomethyl-substituted propargylaldehyde dialkyl acetal. In this special embodiment, with particular preference the hydrazine compound of the formula $R^2HN-NH_2$ and especially methylhydrazine is employed in the form of an aqueous solution.

In an alternative embodiment according to the invention, the compounds of the formula (IV) are provided starting with a propargylaldehyde acetal, by converting the reaction product from step A.1.2c with hydrazine into a compound of the formula (VIII) as defined above, followed by N-alkylation of the compound of the formula (VIII).

With respect to the provision of the reaction product from step A.1.2c, what was said above for the provision of a compound of the formula (V) starting with a propargyl-aldehyde acetal applies. With respect to the reaction of the reaction product with hydrazine to give a compound of the formula (VIII), what was said above for the provision of a compound of the formula (V) from the reaction product applies in a corresponding manner, where, for providing a compound of the formula (VIII), preference is given to using hydrazine sulfate instead of methylhydrazine in the presence of sulfuric acid.

With respect to the N-alkylation of a compound of the formula (VIII), what was said above applies.

This route is particularly preferred if X in the reaction product from step A.1.2c is fluorine; in contrast, the reaction described above of the reaction product from step A.1.2c with a hydrazine compound of the formula $R^2HN-NH_2$ is especially preferred if X is chlorine.

In a further embodiment according to the invention, the provision of a compound of the formula (IV) in which X is fluorine comprises the following steps:
A.1.1d) provision of a compound of the formula (VII)

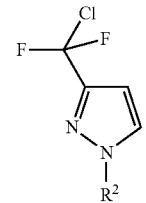

(VII)

in which $R^2$ has one of the meanings given above and
A.1.2d) dechlorination of the compound of the formula (VII).

Methods for the selective removal of chlorine from a difluoromethyl group, here referred to as dechlorination, are described, for example, in Medebielle, Tetrahedron Lett. 2001, 42, 4811 or Harris, Synth. Comm. 1987, 17, 1587. For example, compounds of the formula (VII) can be reacted in the presence of reducing agents, such as Raney nickel or Rongalit ($NaO-S(=O)CH_2OH.2H_2O$), to give compounds of the formula (IV) in which X is fluorine.

As demonstrated above, the compounds of the formula (VII) are suitable in an advantageous manner for the provision according to the invention of compounds of the formula (IV) and thus for the provision according to the invention of compounds of the formula (I). Accordingly, the present invention also provides compounds of the formula (VII).

Compounds of the formula (VII) can be provided, for example, by reacting 4-alkoxy-1-chloro-1,1-difluorobut-3-en-2-ones with a hydrazine compound of the formula $R^2HN-NH_2$, especially methylhydrazine. 4-Alkoxy-1-chloro-1,1-difluorobut-3-en-2-ones can be provided, for example, analogously to the above-described provision of compounds (V) by reacting chlorodifluoroacetyl chloride or chlorodifluoroacetic anhydride instead of dihaloacetyl chlorides with alkyl vinyl ethers.

For the reaction of the compound of the formula (VII) with a hydrazine compound of the formula $R^2HN-NH_2$, especially methylhydrazine, it has been found to be particularly advantageous to use, as solvent, acetic acid. In this special embodiment, the reaction is preferably carried out in the absence of water, i.e. the concentration of water, based on the total amount of solvent, is less than 0.5% by volume. Under these special reaction conditions, reaction of the compound of the formula (VII) with a hydrazine compound of the formula $R^2HN—NH_2$, especially methylhydrazine, is generally carried out without input of thermal energy.

Preferably, the hydrazine compound of the formula $R^2HN—NH_2$ is employed in at least equimolar amounts or in excess. Preferably, from 1.0 to 1.5 mol, in particular from about 1.01 to 1.2 mol, of the hydrazine compound of the formula $R^2HN—NH_2$ are employed per mole of the compound (VII).

In the reaction of the compound (VII) with a hydrazine compound of the formula $R^2HN—NH_2$, the hydrazine compound, preferably as a solution in the organic solvent used for the reaction, is generally added to the compound of the formula (VII) or to a solution thereof in an organic solvent.

In a further embodiment according to the invention, the provision of a compound of the formula (VIII) in which X is F comprises providing a compound of the formula (IX)

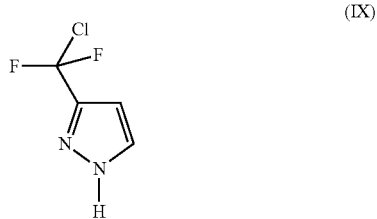

(IX)

and also dechlorinating the compound of the formula (IX).

With respect to the dechlorination of compounds of the formula (IX), what was said regarding the dechlorination of compounds of the formula (VII) applies correspondingly.

As shown, the compounds of the formula (IX) are suitable, in an advantageous manner, for the provision according to the invention of compounds of the formula (VIII) and thus for the provision according to the invention of compounds of the formula (I). Accordingly, the present invention also provides compounds of the general formula (IX).

The provision of compounds of the formula (IX) can be carried out, for example, analogously to the provision of compounds of the formula (VII), where in the respective processes hydrazine is used instead of the hydrazine compound of the formula $R^2HN—NH_2$.

With respect to the preferred reaction conditions for the reaction with hydrazine, what was said above for the reaction of compounds of the formula (V) with hydrazine applies.

In an alternative embodiment, the provision of compounds of the formula (II) in accordance with the present invention comprises A.1') providing a compound of the formula (VI),

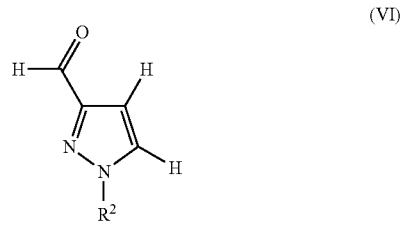

(VI)

in which $R^2$ has one of the meanings given above,

A.2') chlorinating or brominating a compound of the formula (VI) in the 4-position of the pyrazole, giving a compound of the formula (X)

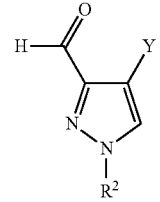

(X)

in which Y is Cl or Br, and also

A.3') converting the carbonyl group of the compound of the formula (X) into a dihalomethyl group.

Compounds of the formula (VI) can be provided, for example, by reacting 4-(dimethylamino)-1,1-dimethoxy-3-en-2-one with a hydrazine compound of the formula $R^2HN—NH_2$ in the presence of a suitable base and subsequent acidic work-up. The reaction is usually carried out in aqueous solution. Suitable bases are, for example, alkali metal hydroxides, such as KOH or NaOH. 4-(Dimethylamino)-1,1-di-methoxy-3-en-2-one can be provided, for example, by reacting a dimethylformamide acetal with methylglyoxal dimethyl acetal.

The bromination of the compound of the formula (VI) is usually carried out using N-bromosuccinimide (NBS) or 1,3-dibromo-5,5-dimethylhydantion (DDH). Correspondingly, the chlorination of the compound of the formula (VI) is carried out with N-chlorosuccinimide (NCS). The use of a polar solvent, such as dimethyl-formamide, N-methylpyrrolidinone, 1,3-dimethyl-2-imidazolidinone, dimethylacetamide, dimethylethyleneurea, dimethylpropyleneurea (DMPU) or tetramethylurea, has been found to be particularly suitable for the halogenation of compounds of the formula (VI). The reaction temperature is usually in a range of from −10 to 80° C. Further reaction conditions for the halogenation which achieve the same objective are known to the person skilled in the art.

For converting the aldehyde group of the compound (VI) into a dihalomethyl group, especially a difluoromethyl group, the reaction, for example, of a compound of the formula (VI), chlorinated or brominated beforehand, with dimethylaminosulfur trifluoride (DAST) has been found to be suitable. This reaction is usually carried out in an inert solvent, such as dichloromethane, at a temperature in the range of from −50 to −10° C., especially at a temperature of about −20° C. DAST is usually employed in an amount of from 2 to 4, preferably from 2.5 to 3, molar equivalents per mole of the previously chlorinated or brominated compound of the formula (VI).

Alternatively, the carbonyl group can be converted by reaction with thionyl chloride in the presence of triphenylphosphine into a dichloromethyl group. If desired, the latter can be converted under the conditions described above for the halogen exchange into a difluoromethyl group.

In a further embodiment according to the invention, the provision of compounds of the formula (II) in which Y is Cl comprises reacting 1,2-dichloroethene with dihaloacetyl chloride in the presence of a Lewis acid, such as $AlCl_3$, to give (Z)-1,1-dihalo-3,4-dihalobut-3-en-2-one, reacting the reaction product obtained with a hydrazine compound of the formula $R^2HN—NH_2$, in which $R^2$ has one of the meanings given above, and the subsequent conversion of the dichloromethyl group by halogen exchange into a difluoromethyl group. With respect to the special embodiments of the reaction with a hydrazine compound of the formula R²HN—NH₂ and to the halogen exchange, reference is made to the relevant sections of the description. These apply correspondingly.

Accordingly, the present invention also provides a process according to the invention in which the provision of a compound of the formula (II) in which Y is Cl comprises A.1") providing a compound of the formula (XI),

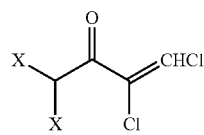
(XI)

in which X is F or Cl,

A.2") reacting a compound of the formula (XI) with a suitable hydrazine compound of the formula R²HN—NH₂ to give a compound of the general formula (II) in which X is F or Cl, Y is Cl and R² has one of the meanings given above, and also A.3") if appropriate, in the case that X in the compound of the formula (II) is chlorine, a halogen exchange for fluorine.

Hereinbelow, the preparation of difluoromethyl-substituted pyrazol-4-ylcarboxamides and their synthesis precursors is illustrated by examples.

EXAMPLES

1. Preparation of N-(2-(3,4,5-trifluorophenyl)-3-difluoromethyl-1-methylpyrazole-4-carboxamide

1.1 Preparation of 1,1-difluoro-4-ethoxy-3-buten-2-one (and 1,1-difluoro-4,4-diethoxy-2-butanone)

At 0° C., difluoroacetyl chloride (41.4 g, 0.36 mol) was added over a period of 37 min from a dropping funnel cooled to −10° C. to ethyl vinyl ether (99% pure, 120 g, 1.375 mol). After 7 h, the mixture was warmed to 22° C. and stirred for a further 12 h. The slightly viscous yellowish reaction mixture (133 g) was then subjected to a flash distillation. This gave 48.5 g of distillate (transition temperature 52-55° C. at 0.4 mbar). A further 30 g was condensed in the cold trap. The distillate contained 1,1-difluoro-4-ethoxy-3-buten-2-one (54.7 GC area %) and 1,1-difluoro-4,4-diethoxy-2-butanone (30.9 GC area %. 10.4 min). The cold trap condensate contained 1,1-difluoro-4-ethoxy-3-buten-2-one (13.2 GC area %) and 1,1-difluoro-4,4-diethoxy-2-butanone (17.1 GC area %).

1,1-Difluoro-4-ethoxy-3-buten-2-one:

EI-MS (GC-MS) [m/z]: 150 [M]⁺; ¹³C-NMR (125 MHz, CDCl₃): δ=14.4, 68.4, 98.9, 110.7, 166.8, 187.4 ppm;

1,1-difluoro-4,4-diethoxy-2-butanone:

EI-MS [m/z]=151; ¹³C-NMR (125 MHz, CDCl₃): δ=15.2, 46.53, 62.55, 98.9, 110.7, 196.5 ppm.

1.2 Preparation of 3-difluoromethyl-N-methylpyrazole

At 22° C., a solution of 45 g of an 85.6% strength mixture comprising 1,1-difluoro-4-ethoxy-3-buten-2-one (0.164 mol) and 1,1-difluoro-4,4-diethoxy-2-butanone (0.071 mol) in a ratio of 2.3/1 in acetic acid (30 ml) was added dropwise over a period of 37 min to a solution of methylhydrazine (99% pure, 11.9 g, 0.258 mol) in acetic acid (460 ml). The resulting reaction solution was stirred at 22° C. for 19 h. The acetic acid was then removed under reduced pressure (43° C./30 mbar). The oily residue was taken up in methyl tert-butyl ether (MTBE, 300 ml) and washed with water (250 ml). The aqueous phase was extracted once with MTBE (150 ml). The collected organic solutions were dried over sodium sulfate, filtered and freed from the solvent under reduced pressure (40° C./400 to 30 mbar). The residue (23.5 g) was subjected to fractional distillation to isolate the product. The main fraction (21.5 g; transition temperature 52° C. at 22 mbar) contained 3-difluoro-N-methylpyrazole and 5-difluoro-N-methylpyrazole in a ratio of 2.6:1 (GC retention times: 5-isomer: 7.6 min; 3-isomer: 9.2 min). Taking into account the amounts of product found in the minor fractions and the cold traps, the yield is 75.5% (sum of both isomers).

¹H-NMR (400 MHz, CDCl₃): δ=3.95 (s, 3H), 6.42 (s, 1H), 6.68 (t, 1H,), 7.4 ppm (s, 1H).

1.3 Preparation of 4-bromo-3-difluoromethyl-1-methylpyrazole

1.3.a) Halogenation with Bromine

At 25° C., bromine (Br₂, 3 g) was added dropwise to a solution of 3-difluoromethyl-N-methylpyrazole (2.0 g) in methylene chloride (80 ml). The reaction mixture was stirred for a total of 22 h at 25° C., and aqueous sodium thiosulfate solution (0.1 M, 210 ml) was then added. After phase separation, the organic phase was freed from the solvent under reduced pressure (40° C./5 mbar). Part of the residue obtained (2.4 g of 2.8 g) was separated by column chromatography (SiO₂, ethyl acetate/cyclohexane 1:6). 4-bromo-3-difluoromethyl-1-methylpyrazole was isolated in an amount of 1.4 g.

EI-MS [m/z]: 210, 212 [M]⁺; ¹H-NMR (400 MHz, CDCl₃): δ=3.9 (s, 3H), 6.68 (t, 1H), 7.43 ppm (s, 1H); ¹³C-NMR (125 MHz, CDCl₃): δ=39.84, 91.47, 110.48, 132.10, 143.54 ppm.

1.3.b) Halogenation with NBS

At 3-5° C., a solution of N-bromosuccinimide (NBS, 7.9 g, 0.04 mol) in dimethylformamide (DMF, 20 ml) was added dropwise (slightly exothermic) to a solution of 3-difluoromethyl-N-methylpyrazole (5.0 g, 0.04 mol) in DMF (40 ml). The reaction mixture was then warmed to room temperature and stirred for a further 2 h. With stirring, the reaction mixture was then added to a mixture of water (200 ml) and aqueous sodium hydroxide solution (conc., 5 ml), and the mixture was extracted four times with methyl tert-butyl ether (MTBE, 100 ml). The combined organic phases were washed with saturated aqueous NaCl solution, dried over magnesium sulfate and filtered, and the solvent was then removed under reduced pressure. This gave 4-bromo-3-difluoromethyl-N-methylpyrazole as an oil (9.5 g; purity: 94.5% (GC analysis); yield 95.2%).

1.4 Preparation of N-(2-(3,4,5-trifluorophenyl)phenyl)-3-difluoromethyl-1-methylpyrazole-4-carboxamide In an autoclave, 2-(3,4,5-trifluorophenyl)aniline (5.29 g, 23.7 mmol), triethylamine (1.20 g, 11.8 mmol), palladium chloride (86 mg, 0.47 mmol), anhydrous potassium carbonate (6.55 g, 47.4 mmol) and 2,2-dimethyl-1,3-bis(diphenylphosphino)propane (313 mg, 0.71 mmol) were added to a solution of 4-bromo-3-difluoromethyl-1-methylpyrazole (5.00 g, 23.7 mmol) in acetonitrile (100 ml). The autoclave was flushed three times with 9 bar of nitrogen and then 3 times with 10 bar of carbon monoxide. The reaction mixture was stirred under a carbon monoxide pressure of 9 mbar at an external temperature of 130° C. for 20 h. The red-brown suspension obtained after cooling and venting was filtered, and the filtrate was freed from volatile components under reduced pressure. The residue was taken up in a mixture of tetrahydrofuran (60 ml) and methyl tert-butyl ether (MTBE, 60 ml), washed twice with hydrochloric acid (5% strength, in each case 40 ml) and once with water (30 ml), dried over sodium sulfate and filtered, and the solvent was removed under reduced pressure. The residue was triturated with diisopropyl ether (20 ml), and the solid was filtered off and dried under reduced pressure. 5.20 g (yield 54%) of N-(2-(3,4,5-trifluorophenyl)phenyl)-3-difluoromethyl-1-methylpyrazole-4-carboxamide were isolated in a purity of 93%, according to HPLC analysis (Merck Chromolith SpeedROD RP-18e column, 50×4.6 mm; gradient: acetonitrile/water with 0.1% trifluoroacetic acid, 7 min from 10% to 95% acetonitrile).

$^1$H-NMR (CDCl$_3$): δ=3.93 (s), 6.65 (t), 7.00 (m), 7.23 (m), 7.42 (m), 7.80 (s, br.), 7.96 (s), 8.20 ppm (m).

2. Palladium-catalyzed preparation of N-(2-(3,4,5-trifluorophenyl)phenyl)-3-difluoromethyl-1-methylpyrazole-4-carboxamide with various phosphine ligands The reactions were carried out in a parallel reactor (Chemspeed Accelerator). The starting materials were weighed in under an atmosphere of nitrogen or added as a solution. At room temperature, the CO partial pressure was ~10 bar. With shaking, the reactor blocks were heated to 130-150° C. During this time, the pressure increased to ~15 bar. After a reaction time of 16 h, cooling and venting of the reaction mixture, decane or diethylene glycol diethyl ether (DEGEE) was added as internal standard, and the reactions were evaluated using the GC area % of the main components.

2.a) Reaction in the presence of 1,3-bis(dicyclohexylphosphino)propane (DCPP)

Pd(C$_6$H$_4$CN)$_2$Cl$_2$ (2.3 mg, 0.0060 mmol), DCPP (7.9 mg, 0.018 mmol), diazabicycloundecene (DBU, 274.0 mg, 1.8 mmol), 4-bromo-3-difluoromethyl-1-methylpyrazole (253.3 mg, 1.2 mmol) and 2-(3,4,5-trifluorophenyl)aniline (267.8 mg, 1.2 mmol) were weighed in under protective gas. Dimethylformamide (DMF, 5 ml) was added under argon. The reaction mixture was shaken for 10 min. The reaction mixture was then shaken vigorously at a CO pressure of 15 bar and a temperature of 130° C. for 16 h. After cooling of the reaction mixture, DEGEE (0.2 ml) was added as an internal standard for the GC analysis.

Result of the GC analysis [area %]: 58.36 DMF; 4.14 DEGEE; 1.16 4-bromo-3-difluoromethyl-1-methylpyrazole; 0.11 2-(3,4,5-trifluorophenyl)aniline; 12.92 N-(2-(3,4,5-trifluorophenyl)phenyl)-3-difluoromethyl-1-methylpyrazole-4-carboxamide.

This corresponds to a formal yield of >90%.

2.b) Reaction in the presence of 1,1'-bis(diphenylphosphino)ferrocene (DPPF)

Pd(C$_6$H$_4$CN)$_2$Cl$_2$ (2.3 mg, 0.0060 mmol), DPPF (10.0 mg, 0.018 mmol), triethylamine (91.1 mg, 0.9 mmol), potassium carbonate (124.4 mg, 0.9 mmol), 4-bromo-3-difluoromethyl-1-methylpyrazole (253.3 mg, 1.2 mmol) and 2-(3,4,5-trifluoro-phenyl)aniline (267.8 mg, 1.2 mmol) were weighed in under protective gas. Acetonitrile (5 ml) was added under argon, and the resulting reaction mixture was shaken for 10 min. The reaction mixture was then shaken vigorously at a CO pressure of 15 bar and a temperature of 130° C. for 16 h. After cooling of the reaction mixture, DEGEE (0.2 ml) was added as internal standard for the GC analysis.

Result of the GC analysis [area %]: 76.49 acetonitrile; 3.87 DEGEE; 0.00 4-bromo-3-difluoromethyl-1-methylpyrazole; 2.10 2-(3,4,5-trifluorophenyl)aniline; 12.25 N-(2-(3,4,5-trifluorophenyl)phenyl)-3-difluoromethyl-1-methylpyrazole-4-carboxamide.

This corresponds to a formal yield of >85%.

2.c) Reaction in the presence of 1,3-bis(di-(2,6-dimethoxyphenyl)phosphino)propane ((o-MeO)-DPPP)

Pd(C$_6$H$_4$CN)$_2$Cl$_2$ (23 mg, 0.0060 mmol), (o-MeO)-DPPP (9.6 mg, 0.018 mmol), potassium carbonate (248.8 mg, 1.8 mmol), 4-bromo-3-difluoromethyl-1-methylpyrazole (253.3 mg, 1.2 mmol) and 2-(3,4,5-trifluorophenyl)aniline (26.8 mg, 1.2 mmol) were weighed in under protective gas. N-methylpyrrolidone (NMP, 5 ml) was added under argon. The reaction mixture was shaken for 10 min. The reaction mixture was then shaken vigorously at a CO pressure of 15 bar and a temperature of 130° C. for 16 h. After cooling of the reaction mixture, DEGEE (0.2 ml) was added as internal standard for the GC analysis.

Result of the GC analysis [area %]: 83.14 NMP; 1.25 DEGEE; 0.17 4-bromo-3-difluoromethyl-1-methylpyrazole; 3.15 2-(3,4,5-trifluorophenyl)aniline; 2.87 N-(2-(3,4,5-trifluorophenyl)phenyl)-3-difluoromethyl-1-methylpyrazole-4-carboxamide.

This corresponds to a formal yield of >34%.

2.d) Reaction in the presence of 1,3-bis(dicyclohexylphosphino)propane (DCPP)

Pd(C$_6$H$_4$CN)$_2$Cl$_2$ (2.3 mg, 0.0060 mmol), DCCP (7.9 mg, 0.018 mmol), triethylamine (91.1 mg, 0.9 mmol), potassium carbonate (124.4 mg, 0.9 mmol), 4-bromo-3-difluoromethyl-1-methylpyrazole (253.3 mg, 1.2 mmol) and 2-(3,4,5-trifluoro-phenyl)aniline (26.8 mg, 1.2 mmol) were weighed in under protective gas. Acetonitrile (MeCN, 5 ml) was added under argon. The reaction mixture was shaken for 10 min. The reaction mixture was then shaken vigorously at a CO pressure of 15 bar and a temperature of 130° C. for 16 h. After cooling of the reaction mixture, DEGEE (0.2 ml) was added as internal standard for the GC analysis.

Result of the GC analysis [area %]: 76.10 MeCN; 3.86 DEGEE; 1.20 4-bromo-3-difluoromethyl-1-methylpyrazole; 4.26 2-(3,4,5-trifluorophenyl)aniline; 8.54 N-(2-(3,4,5-trifluorophenyl)phenyl)-3-difluoromethyl-1-methylpyrazole-4-carboxamide.

This corresponds to a formal yield of >61%.

2.e) Reaction in the presence of 2-butyl-2-ethyl-1,3-bis(diphenylphosphino)propane (Bustar, Et,Bu-Pepstar)

Pd(C$_6$H$_4$CN)$_2$Cl$_2$ (2.3 mg, 0.0060 mmol), Bustar (8.9 mg, 0.018 mmol), triethylamine (91.1 mg, 0.9 mmol), potassium carbonate (124.4 mg, 0.9 mmol), 4-bromo-3-difluoromethyl-1-methylpyrazole (253.3 mg, 1.2 mmol) and 2-(3,4,5-trifluorophenyl)aniline (26.8 mg, 1.2 mmol) were weighed in under protective gas. Acetonitrile (MeCN, 5 ml) was added under argon. The reaction mixture was shaken for 10 min. The reaction mixture was then shaken vigorously at a CO pressure of 15 bar and a temperature of 130° C. for 16 h. After cooling of the reaction mixture, DEGEE (0.2 ml) was added as internal standard for the GC analysis.

Result of the GC analysis [area %]: 77.50 MeCN; 3.88 DEGEE; 0.04 4-bromo-3-difluoromethyl-1-methylpyrazole; 3.23 2-(3,4,5-trifluorophenyl)aniline; 9.89 N-(2-(3,4,5-trifluorophenyl)phenyl)-3-difluoromethyl-1-methylpyrazole-4-carboxamide.

This corresponds to a formal yield of >70%

2.f) Reaction in the presence of 1,3-bis(di-(2,6-dimethoxyphenyl)phosphino)propane (o-MeO-DPPP)

$Pd(C_6H_4CN)_2Cl_2$ (2.3 mg, 0.0060 mmol), o-MeO-dppp (9.6 mg, 0.018 mmol), potassium phosphate (382.1 mg, 1.8 mmol), 4-bromo-3-difluoromethyl-1-methylpyrazole (25.3 mg, 1.2 mmol) and 2-(3,4,5-trifluorophenyl)aniline (26.8 mg, 1.2 mmol) were weighed in under protective gas. Dimethylacetamide (DMA, 5 ml) was added under argon. The reaction mixture was shaken for 10 min. The reaction mixture was then shaken vigorously at a CO pressure of 15 bar and a temperature of 130° C. for 16 h. After cooling of the reaction mixture, DEGEE (0.2 ml) was added as internal standard for the GC analysis.

Result of the GC analysis [area %]: 80.12 DMA; 3.74 DEGEE; 1.50 4-bromo-3-difluoromethyl-1-methylpyrazole; 3.34 2-(3,4,5-trifluorophenyl)aniline; 8.00 N-(2-(3,4,5-trifluorophenyl)phenyl)-3-difluoromethyl-1-methylpyrazole-4-carboxamide.

This corresponds to a formal yield of >62%

2.g) Reaction in the presence of 2,2-dimethyl-1,3-bis(diphenylphosphino)propane (Pepstar)

$Pd(C_6H_4CN)_2Cl_2$ (2.3 mg, 0.0060 mmol), Pepstar (7.9 mg, 0.018 mmol), potassium carbonate (248.8 mg, 1.8 mmol), 4-bromo-3-difluoromethyl-1-methylpyrazole (253.3 mg, 1.2 mmol) and 2-(3,4,5-trifluorophenyl)aniline (26.8 mg, 1.2 mmol) were weighed in under protective gas. N-methylpyrrolidone (NMP, 5 ml) was added under argon. The reaction mixture was shaken for 10 min. The reaction mixture was then shaken at a CO pressure of 15 bar and a temperature of 130° C. for 16 h. After cooling of the reaction mixture, DEGEE (0.2 ml) was added as internal standard for the GC analysis.

Result of the GC analysis [area %]: 17.98 NMP; 6.13 DEGEE; 2.11 4-bromo-3-difluoromethyl-1-methylpyrazole; 3.76 2-(3,4,5-trifluorophenyl)aniline; 13.48 N-(2-(3,4,5-trifluorophenyl)phenyl)-3-difluoromethyl-1-methylpyrazole-4-carboxamide.

This corresponds to a formal yield of >70%

2.h) Reaction in the presence of 1-[2-(bis(ethyl)phosphino)ferrocenyl]ethyl-di-tert-butylphosphine (Josiphos $tBu_2P$-Fc-$PEt_2$)

$Pd(C_6H_4CN)_2Cl_2$ (2.3 mg, 0.0060 mmol), Josiphos $tBu_2P$-Fc-$PEt_2$ (10.4 mg, 0.018 mmol), DBU (274.0 mg, 1.8 mmol), 4-bromo-3-difluoromethyl-1-methylpyrazole (253.3 mg, 1.2 mmol) and 2-(3,4,5-trifluorophenyl)aniline (26.8 mg, 1.2 mmol) were weighed in under protective gas. Dimethylformamide (DMF, 5 ml) was added under argon. The reaction mixture was shaken for 10 min. The reaction mixture was then shaken at a CO pressure of 15 bar and a temperature of 130° C. for 16 h. After cooling of the reaction mixture, DEGEE (0.2 ml) was added as internal standard for the GC analysis.

Result of the GC-analysis [area %]: 58.85 DMF; 4.48 DEGEE; 0.37 4-bromo-3-difluoromethyl-1-methylpyrazole; 4.34 2-(3,4,5-trifluorophenyl)aniline; 9.66 N-(2-(3,4,5-trifluorophenyl)phenyl)-3-difluoromethyl-1-methylpyrazole-4-carboxamide.

This corresponds to a formal yield of >67%.

2.i) Study on the effect of the CO pressure on the reaction in the presence of 2,2-dimethyl-1,3-bis(diphenylphosphino)propane (Pepstar)

A solution of $Pd(PhCN)_2Cl_2$ (0.0375 mmol) and Pepstar (0.1125 mmol) in dimethyl-formamide (DMF, 5 ml) was stirred at room temperature for 30 minutes. The solution comprising the pre-formed catalyst was transferred into an inertized autoclave. In a CO countercurrent, a solution of diazabicycloundecene (DBU, 16.5 mmol), 3-difluoro-methyl-1-methyl-4-bromopyrazole (15 mmol) and 2-(3,4,5-trifluorophenyl)aniline (15 mmol) in DMF (40 ml) was added to the solution of the catalyst in the autoclave. The reaction was carried out with stirring at 150° C. and the CO pressure stated in table 1 until the bromopyrazole had been converted completely.

TABLE 1

Tests on carbonylation at various CO pressures

| Experiment | CO pressure [bar] | Reaction time [h] | Isolated yields [%] |
|---|---|---|---|
| 2.i.1 | 10 | 20 | 81 |
| 2.i.2 | 15 | 20 | 68 |
| 2.i.3 | 25 | 18.5 | 70 |
| 2.i.4 | 30 | 20 | 66 |
| 2.i.5 | 40 | 32 | 21 |

After the reaction had ended, methyl tert-butyl ether (MTBE, 50 ml) was added, and the reaction mixture was washed with water (30 ml). The aqueous phase was extracted with MTBE (4×30 ml). The organic phases were then combined, dried and freed from the solvent under reduced pressure.

The residue was dissolved in toluene (10 ml) and warmed with stirring. n-Hexane (10 ml) was then added. After a few minutes, crystals formed which were filtered off after 1 h, washed with hexane and dried. The filtrate was concentrated, the residue formed was dissolved in toluene and n-hexane was added. In this manner, it was possible to isolate more product from the filtrate.

The reaction times required for complete conversion and the yields isolated in the reaction are shown in table 1.

$^1$H-NMR (499.8 MHz) $CDCl_3$, internal standard: TMS): d=3.87 (s, 3 H), 6.71 (t, J=54.2 Hz, 1 H); 6.98 (m, 2 H), 7.25 (m, 2 H) 7.39 (m, 1 H), 7.91 (br s, 2 H) 8.08 ppm (d, J=8.2, 1 H).

$^{13}$C-NMR (125.7 MHz, $CDCl_3$, TMS as internal standard): d=39.51 (s), 111.5 (t, J=233.2 Hz), 113.60 (ddd, J=16.2 Hz, J=5.32 Hz), 116.52 (s), 123.79 (s), 125.41 (s), 129.22 (s), 130.11 (s), 131.58 (td, J=1.0 Hz), 134.29 (td, J=7.0 Hz, J=5.0 Hz), 134.51 (s), 135.9 (s), 135.85 (s), 139.53 (dt, J=252.4 Hz, J=15.1 Hz), 142.7 (t, J=28.9 Hz), 151.3 (ddd, J=251.0 Hz, J=9.9 Hz, J=4.1 Hz) 159.65 ppm (s).

2.k) Reaction in the presence of 2,2-dimethyl-1,3-bis(diphenylphosphino)propane (Pepstar)

A solution of Pd(PhCN)$_2$Cl$_2$ (0.008 mmol) and Pepstar (0.024 mmol) in dimethyl-formamide (DMF, 5 ml) was stirred at room temperature for 30 minutes. The solution comprising the pre-formed catalyst was transferred into an inertized autoclave. In a CO countercurrent, diazabicycloundecene (DBU, 8.8 mmol), tetrabutylammonium bromide (0.32 mmol) and solutions of 3-difluoromethyl-1-methyl-4-bromopyrazole (8.8 mmol) and 2-(3,4,5-trifluorophenyl)aniline (8 mmol) in DMF (20 ml each) were added to the solution of the catalyst in the autoclave. The reaction mixture was stirred at 150° C. and a CO pressure of 15 bar for 24 h.

The conversion, based on 2-(3,4,5-trifluorophenyl)aniline, was 76%, at a selectivity of 100%. The composition of the reaction discharge was, according to GC analysis, as follows: DMF 78.65 area %, 3-difluoromethyl-1-methyl-4-bromopyrazole 0.0 area %, DBU 12.98 area %, 2-(3,4,5-trifluorophenyl)aniline 1.99 area % and N-(2-(3,4,5-trifluorophenyl)phenyl)-3-difluoromethyl-1-methylpyrazole-4-carboxamide 6.38 area %.

Work-up was carried out as described in example 2.i), giving an isolated yield of N-(2-(3,4,5-trifluorophenyl)phenyl)-3-difluoromethyl-1-methylpyrazole-4-carboxamide of 45.4%.

2.l) Reaction in the presence of 2-butyl-2-ethyl-1,3-bis(diphenylphosphino)propane (Bustar)

A solution of Pd(PhCN)$_2$Cl$_2$ (0.0375 mmol) and Bustar (0.1125 mmol) in dimethyl-formamide (DMF, 10 ml) was stirred at room temperature for 30 minutes. The solution comprising the pre-formed catalyst was transferred into an inertized autoclave. In a CO countercurrent, diazabicycloundecene (DBU, 16.5 mmol) and solutions of 3-difluoro-methyl-1-methyl-4-bromopyrazole (16.5 mmol) and 2-(3,4,5-trifluorophenyl)aniline (15 mmol) in DMF (25 ml each) were added to the solution of the catalyst in the autoclave. The reaction mixture was stirred at 150° C. and a CO pressure of 15 bar for 24 h.

The conversion, based on 2-(3,4,5-trifluorophenyl)aniline, was 99% at a selectivity of 94%. The composition of the reaction discharge was, according to GC analysis, as follows: DMF 44.6 area %, bromopyrazole 0.1 area %, DBU 29.7 area %, 2-(3,4,5-trifluorophenyl)aniline 0.3 area % and N-(2-(3,4,5-trifluorophenyl)phenyl)-3-difluoro-methyl-1-methylpyrazole-4-carboxamide 22.7 area %.

Work-up was carried out as described in example 2.i), giving an isolated yield of N-(2-(3,4,5-trifluorophenyl)phenyl)-3-difluoromethyl-1-methylpyrazole-4-carboxamide of 78%.

3. Preparation of 3-difluoromethyl-N-methylpyrazole by reaction of 3-difluoromethyl-NH-pyrazole with hydrazine and subsequent N-methylation

3.1 Preparation of 3-difluoromethyl-NH-pyrazole

At a temperature of from 22 to 31° C., a solution of 1 g of an 86% pure mixture comprising 1,1-difluoro-4-ethoxy-3-buten-2-one and 1,1-difluoro-4,4-diethoxy-2-butanone in a ratio of 1.5:1 in acetic acid (3 ml) was added dropwise over a period of 26 min to a solution of hydrazine hydrate (100% pure, 0.31 g, 0.063 mol) in acetic acid (10 ml). The solution was stirred at 22° C. for 64 h. The acetic acid was then distilled off (42° C./30 mbar). The oily residue was taken up in methyl tert-butyl ether (MTBE, 4 ml) and washed three times with water (10 ml). A sample of the MTBE solution was concentrated under reduced pressure (39° C./25 mbar, and then 0.4 mbar).

EI-MS (GC-MS) [m/z]: 118 [M]$^+$; $^1$H-NMR (400 MHz, CDCl$_3$): δ=6.65 (s, 1H), 6.8 (t, 1H), 7.68 (s, 1H), 10.2 ppm (s, broad, NH); $^{13}$C-NMR (125 MHz, CDCl$_3$): δ=103.41, 111.09, 130.22, 146.41 ppm.

3.2 Preparation of 3-difluoromethyl-N-methylpyrazole a) At 22° C., an acetic acid solution (40 ml) of 59 g of a 77.4% pure mixture comprising 1,1-difluoro-4-ethoxy-3-buten-2-one (0.145 mol) and 1,1-difluoro-4,4-diethoxy-2-butanone (0.122 mol) in a ratio of 1.1/1 was added dropwise over a period of 76 min to a solution of hydrazine hydrate (14.7 g, 0.294 mol) in acetic acid (600 ml). The solution was stirred at 22° C. for 16 h. The acetic acid was then removed under reduced pressure (45° C./28 mbar). The oily residue was taken up in ethyl acetate (450 ml) and washed with water (450 ml). The aqueous phase was reextracted once with ethyl acetate (250 ml). The turbid aqueous phase was filtered through kieselguhr. The kieselguhr was washed with a little ethyl acetate, and the aqueous phase was reextracted again with MTBE (250 ml). The combined organic solutions were dried over sodium sulfate and filtered, and volatile components were removed under reduced pressure. A residue of 41.5 g remained.

b) Part of the residue (37.4 g, 0.24 mol) was dissolved in acetone (540 ml). Potassium carbonate (57.4 g) was added to the solution. Dimethyl sulfate (52.4 g, 0.42 mol) was then added dropwise over a period of 73 minutes. During this time, the reaction mixture warmed to 31° C. The reaction mixture was then stirred at a temperature of 28.5 to 30° C. for 105 min, at 21° C. for a further 18 h and at 29 to 37° C. for a further 75 min. The reaction mixture contained 2.7% (GC area) of starting material and 6.8% (GC area) of dimethyl sulfate. About 390 g of acetone were then removed on a rotary evaporator (40° C./300 mbar). The residue was taken up in water (300 ml) and ethyl acetate (200 ml). After phase separation, the aqueous phase was extracted with ethyl acetate (100 ml). The combined organic phases were dried over sodium sulfate (30 g) and filtered, and the solvent was removed under reduced pressure (40° C./400 to 300 mbar). The residue (40.6 g) is subjected to fractional distillation to isolate the product. The main fraction (20.4 g, transition temperature 20-65° C. at 20 mbar) contained 3-difluoro-N-methylpyrazole and 5-difluoro-N-methylpyrazole in a ratio of 4.7:1 (GC retention times: 5-isomer: 7.6 min; 3-isomer: 9.2 min).

Yield over steps a) and b) (after distillation): 47% (sum of both isomers). If the amounts of product found in the minor fractions and cold traps are taken into account, a corrected yield of 58% results.

3-Difluoromethyl-N-methylpyrazole:
$^1$H-NMR (400 MHz, CDCl$_3$): δ=3.95 (s, 3H), 6.42 (s, 1H), 6.68 (t, 1H), 7.4 ppm (s, 1H);
5-difluoromethyl-N-methylpyrazole:
$^1$H-NMR (400 MHz, CDCl$_3$): δ=4.95 (s, 3H), 6.42 (s, 1H), 6.68 (t, 1H), 7.4 ppm (s, 1H).

The 3-difluoromethyl-N-methylpyrazole obtained in this manner can be used for example 1.

4. Preparation of 3-dichloromethyl-N-methylpyrazole via in-situ-preparation of 1,1-dichloro-4-ethoxy-3-buten-2-one Under reflux conditions (38° C.), dichloroacetyl chloride (98% pure, 30.2 g, 0.2 mol) was added to ethyl vinyl ether (200 ml, about 2.09 mol). After 3 h, about 60 ml of excess ethyl vinyl ether were distilled off at 50° C. Toluene (100 ml) was then added. Volatile components were removed together with toluene under reduced pressure (50° C./60 mbar). More toluene (100 ml) was added to the residue. The yellowish solution prepared in this manner was heated to reflux temperature. With simultaneous distillative removal of the toluene, a solution of methylhydrazine (98% pure, 9.4 g, 0.2 mol) in toluene (100 ml) was then added dropwise over a period of 70 min. At the same time, toluene was added continuously to the reaction mixture, in an amount corresponding to the volume obtained as distillate. After a further 30 min of stirring, the mixture was cooled to 25° C. and washed with water (1×100 ml and 1×50 ml). The aqueous phases were extracted with methylene chloride (2×100 ml). The organic phases were combined, and the solvent was removed under reduced pressure (50° C./15 mbar). The residue (25.3 g) was separated by flash distillation. The distillate obtained (12.9 g, transition temperature 56-60° C./0.3 to 0.2 mbar) was an isomer mixture of 3-dichloromethyl-N-methylpyrazole and 5-dichloromethyl-N-methylpyrazole in a ratio of 80:20 (GC area %). This corresponds to a yield of 3-dichloromethyl-N-methylpyrazole of 36%.

4a. Preparation of 1,1-dichloro-4-ethoxy-3-buten-2-one

At about 0° C., dichloroacetyl chloride (95% pure, 16.5 g, 0.11 mol) and ethyl vinyl ether (99% pure, 48.7 g, 0.67 mol) were added and stirred for 5 h. The mixture was then stirred at 22° C. for about 11 h. Most of the excess ethyl vinyl ether was then removed by distillation under reduced pressure (40° C./300-400 mbar). The product was separated off from the residue (18.7 g) by flash distillation (oil bath 100° C./0.7 mbar; transition 72° C.). The distillate obtained was a product mixture (15.6 g). This consisted to 80% (GC area %) of the desired product. Furthermore, the product mixture consisted to about 5% (GC area %) of 1,1-dichloro-4,4-diethoxy-2-butanone. Including the corresponding diethyl acetal, the yield was about 68%.

The 1,1-dichloro-4-ethoxy-3-buten-2-one obtained in this manner can be converted, for example, analogously to example 3 by reaction with methylhydrazine into 3-dichloromethyl-N-methylpyrazole.

5. Preparation of 3-dichloromethyl-N-methylpyrazole from 1,1,4-trichloro-3-buten-2-one At 20° C., 1,1,4-trichloro-3-buten-2-one (15 g, 0.078 mol) was added dropwise over a period of 37 min to a solution of 1,1-dimethylhydrazine (9.5 g, 0.156 mol) in methyl tert-butyl ether (MTBE, 500 ml), with warming to 34° C. After 2 h, a sticky brown suspension had formed, which was filtered through kieselguhr. The filtrate was concentrated under reduced pressure. The residue (7.6 g of a viscous oil) was subjected to fractional distillation under reduced pressure. As the main fraction, 3 g of 3-dichloromethyl-N-methylpyrazole were obtained in a purity of 96.4% (GC area) (boiling point 65° C./0.3 mbar), and the product crystallized on standing. Recrystallization gave a sample having a purity of >99% (GC area).

m.p.: 38.5-40° C.; $^1$H-NMR (400 MHz, CDCl$_3$): δ=3.88 (s, 3H), 6.5 (s, 1H), 6.8 (s, 1H), 7.34 ppm (s, 1H); $^{13}$C-NMR (125 MHz, CDCl$_3$): δ=65.24, 104.10, 131.60, 151.50 ppm.

6. Preparation of 3-dichloromethyl-N-methylpyrazole via in-situ-preparation of 1,1-dichloro-4-ethoxy-3-buten-2-one and reaction with methylhydrazine At 10° C., dichloroacetyl chloride (98% pure, 15.1 g, 0.1 mol) was added to ethyl vinyl ether (100 ml, about 1.04 mol). After 16 h, about 30 ml of the excess ethyl vinyl ether was distilled off at 50° C. Toluene (100 ml) was then added, and volatile components were coevaporated with toluene under reduced pressure (50° C./60 mbar). The residue was dissolved in toluene (about 100 ml). Acetic acid (100 ml) was added to this solution. With warming to 30° C., an aqueous methylhydrazine solution (40% strength, 11.5 g, 0.1 mol) was then added dropwise over a period of 15 min. A 2-phase mixture was formed, which was stirred at 25° C. for a further 12 h. The phases were then separated and the toluene was distilled off under reduced pressure (50° C./10 mbar). The residue was taken up in toluene (100 ml) and reconcentrated. The residue obtained was 12.0 g of an isomer mixture of 3-dichloromethyl-N-methylpyrazole and 5-dichloromethyl-N-methylpyrazole in a ratio of 57:43 (GC area %).

7. Preparation of 3-dichloromethyl-NH-pyrazole from 1,1-dichloro-4-ethoxy-3-buten-2-one At 22° C., a solution of 36.4 g of a mixture comprising 1,1-dichloro-4-ethoxy-3-buten-2-one (0.154 mol) and 1,1-dichloro-4,4-diethoxy-2-butanone (21.5 mmol), in acetic acid (20 ml) was added dropwise over a period of 50 min to a solution of hydrazine hydrate (9.7 g, 0.193 mol) in acetic acid (100 ml). The solution was stirred at 22° C. for 20 h. The acetic acid was then removed by distillation (42° C./25 mbar, then 0.2 mbar). The oily residue was taken up in methyl tert-butyl ether (MTBE, 150 ml) and washed three times with water (30 ml). The organic phase was filtered over kieselguhr. The filtrate was concentrated (39° C./400 to 25 mbar, then 0.4 mbar).

This gave 27 g of a crude product which still contained about 9% of acetic acid. This crude product was used without further purification for the subsequent reactions.

EI-MS (GC-MS) [m/z]: 150 [M]$^+$; $^1$H-NMR (400 MHz, CDCl$_3$): δ=6.65 (s, 1H), 6.9 (s, 1H), 7.75 (s, 1H), 10.5 ppm (s, broad, 1H); $^{13}$C-NMR (125 MHz, CDCl$_3$): δ=66.16, 102.76, 130.35, 150.31 ppm.

8. Preparation of 3-difluorochloromethyl-NH-pyrazole from 4-butoxy-1-chloro-1,1-difluorobut-3-en-2-one Over a period of 10 minutes, hydrazine hydrate (80% pure, 0.52 g, 0.008 mol) was added dropwise to a solution of 4-butoxy-1-chloro-1,1-difluorobut-3-en-2-one (1.2 g, 0.005 mol) in ethanol (6 ml). The mixture was then stirred under reflux conditions for 5 h. The resulting yellow-brown suspension was concentrated on a rotary evaporator. The residue was taken up in ethyl acetate (20 ml) and water (20 ml). After separation of the phases, the aqueous phase was re-extracted with ethyl acetate (20 ml). The organic phases were combined, dried over MgSO$_4$ and filtered, and volatile components were removed under reduced pressure. The light-red oily residue (0.35 g) consisted to about 65% of 3-difluorochloromethyl-NH-pyrazole and to 35% of ethyl pyrazole-3-carboxylate.

3-Difluorochloromethyl-NH-pyrazole: EI-MS [m/z]: 152 [M]$^+$; $^1$H-NMR (500 MHz, CDCl$_3$): δ=6.68 (s, 1H), 7.9 (s, 1H), 11.5-13.5 ppm (s, broad, NH); $^{13}$C-NMR (125 MHz, CDCl$_3$): δ=103.61, 124.76, 131.18, 147.91 ppm.

Ethyl pyrazole-3-carboxylate: EI-MS [m/z]: 140 [M]$^+$; $^1$H-NMR (500 MHz, CDCl$_3$): δ=1.38 (t, 3H), 4.32 (q, 2H), 6.8 (s, 1H), 7.8 (s, 1H), 11.5-13.5 ppm (s, broad, NH); $^{13}$C-NMR (125 MHz, CDCl$_3$): δ=14.24, 60.2, 107.80, 132.30, 141.00, 161.60 ppm.

9. Preparation of 3-difluorochloromethyl-N-methylpyrazole from 4-butoxy-1-chloro-1,1-difluorobut-3-en-2-one Over a period of 20 min, a solution of 4-butoxy-1-chloro-1,1-difluorobut-3-en-2-one (2 g, 0.009 mol) in toluene (5 ml) was added dropwise to a solution of methylhydrazine (0.43 g, 0.009 mol) in toluene (15 ml). The reaction is slightly exothermic. The reaction mixture is then stirred at 0° C. for 30 min. A GC sample shows complete conversion into 2 new products. In addition, n-butanol is detected. The reaction mixture is then stirred at room temperature for a further 2 days. The yellow reaction solution is then concentrated on a rotary evaporator. The oily residue (1.4 g) is taken up in toluene, a spatula tip of p-toluene sulfonic acid (0.1 g) is added and the mixture is stirred at 80° C. for 1.5 h. The reaction mixture is then washed successively with a saturated aqueous NaHCO$_3$ solution (20 ml) and with water (20 ml). Concentration of the organic phase gave, as a residue, a yellow oil (0.3 g).

EI-MS [m/z]: 166 [M]$^+$; $^1$H-NMR (500 MHz, CDCl$_3$): δ=3.95 (s, 3H), 6.55 (s, 1H), 7.72 ppm (s, 1H); $^{13}$C-NMR (125 MHz, CDCl$_3$): δ=147.20, 104.35, 133.10, 39.65, 124.44 ppm.

10. Preparation of 3-difluorochloromethyl-N-methylpyrazole from 4-butoxy-1-chloro-1,1-difluorobut-3-en-2-one Over a period of 30 minutes, a solution of methylhydrazine (1.6 g, 0.034 mol) in acetic acid (10 ml) was added dropwise to a solution of 4-butoxy-1-chloro-1,1-difluorobut-3-en-2-one (80% pure, 8 g, 0.03 mol) in acetic acid (60 ml). The reaction is slightly exothermic. The solution was stirred at 25° C. for about 16 h. The reaction solution was then concentrated under reduced pressure (50° C./30 mbar). GC-analysis of the residue showed an isomer ratio of 11:1 in favor of the 3-isomer (GC retention times: 4.3 min (5-isomer); 8.2 min (3-isomer)). Methyl tert-butyl ether (MTBE, 20 ml) and water (20 ml) were added to the residue. After phase separation, the organic phase was dried over sodium sulfate and filtered, and volatile components were removed under reduced pressure (50° C./30 mbar). The oily residue (3.7 g) was examined by GC analysis. The areas of the two isomers corresponded to 73% of the total GC area and were present in a ratio of 49:1 in favor of the 3-isomer. The yield was about 58%.

EI-MS (GC-MS) [m/z]: 166 [M]$^+$.

11. Preparation of 3-difluorochloromethyl-NH-pyrazole from 4-butoxy-1-chloro-1,1-difluorobut-3-en-2-one Over a period of 30 minutes, a solution of hydrazine hydrate (1.7 g, 0.034 mol) in acetic acid (10 ml) was added dropwise to a solution of 4-butoxy-1-chloro-1,1-difluorobut-3-en-2-one (80% pure, 8 g, 0.03 mol) in acetic acid (60 ml). The reaction was slightly exothermic. The reaction mixture was stirred at 25° C. for about 16 h. The reaction mixture was then freed from volatile components (50° C./30 mbar). Methyl tert-butyl ether (MTBE, 20 ml) and water (20 ml) were added to the residue. After phase separation, the organic phase was dried over sodium sulfate and filtered, and the solvent was removed (50° C./30 mbar). According to GC analysis, the oily residue (5.1 g) consisted to 80% of 3-difluorochloromethyl-NH-pyrazole (GC retention time: 11.9 min). This corresponds to a yield of 89%.

12. Preparation of 1-methylpyrazole-3-carbaldehyde from 4-(dimethylamino)-1,1-dimethoxybut-3-en-2-one With cooling, methylhydrazine (151.3 g, 3.29 mol) was added dropwise to a solution of NaOH (131.4 g, 3.29 mol) in water (1700 ml). 4-(Dimethylamino)-1,1-dimethoxybut-3-en-2-one (569 g, 3.28 mol) was then added dropwise at room temperature, and the mixture was stirred overnight. Hydrochloric acid (36% strength, 219.6 g, 2.17 mol) was added, and the reaction mixture was stirred for 4 h. Using aqueous sodium hydroxide solution (10% strength), the reaction mixture was then adjusted to a pH of 9.4. After four extractions with methylene chloride (500 ml), the organic phases were washed with water, dried over magnesium sulfate and filtered, and the solvent was removed under reduced pressure. According to GC analysis, the oily residue had a purity of 73%. In addition to the desired 1-methylpyrazole-3-carbaldehyde, the residue contained, as a byproduct, 10.7% of the 5-carbaldehyde. This was removed by distillation under reduced pressure (transition temperature: 55° C. at 2.5 to 2.3 mbar). The yield of 1-methylpyrazole-3-carbaldehyde was 53%.

$^1$H-NMR (CDCl$_3$): δ=4.05 (s, 3H) 6.8 (s, 1H), 7.5 (s, 1H), 9.95 ppm (s, 1H).

13. Preparation of 4-bromo-3-dichloromethyl-1-methylpyrazole from 1-methylpyrazole-3-carbaldehyde

13.1 Preparation of 4-bromo-1-methylpyrazole-3-carbaldehyde by bromination of 1-methylpyrazole-3-carbaldehyde At 3-5° C., a solution of N-bromosuccinimide (NBS, 64.6 g, 0.36 mol) in dimethyl-formamide (DMF, 160 ml) was added dropwise (slightly exothermic) to a solution of 1-methylpyrazole-3-carbaldehyde (40 g, 0.36 mol) in DMF (320 ml). The reaction mixture was then heated to room temperature and stirred for a further 2 h. The reaction mixture was then added with stirring to a mixture of water (1400 ml) and aqueous sodium hydroxide solution (conc., 15 ml) and extracted four times with methyl tert-butyl ether (MTBE, 100 ml). The organic phases were combined and washed with saturated NaCl solution, dried over magnesium sulfate and filtered, and the solvent was then removed under reduced pressure. This gave 4-bromo-1-methylpyrazole-3-carbaldehyde as a solid (42.9 g, 98% pure according to GC analysis, yield 61.3%).

$^1$H-NMR (CDCl$_3$): δ=4.0 (s, 3H), 7.55 (s, 1H), 9.95 ppm (s, 1H); $^{13}$C-NMR (CDCl$_3$): δ=40.3, 95.1, 133.0, 146.5, 184.6 ppm.

13.2 Preparation of 4-bromo-3-dichloromethyl-1-methylpyrazole from 4-bromo-1-methylpyrazole-3-carbaldehyde 4-Bromo-1-methylpyrazole-3-carbaldehyde (4.0 g, 0.02 mol) was initially charged together with triphenylphosphine (5.9 g, 0.022 mol) in chlorobenzene (40 ml). Thionyl chloride (2.6 g, 0.022 mol) was then added dropwise at room temperature. After the addition had ended, the reaction mixture was warmed to 50° C. for one hour and stirred at room temperature overnight. Ice (40 g) was then added, and the mixture was extracted twice with methylene chloride (100 ml). The organic phases were dried over magnesium sulfate and filtered, and the solvent was removed under reduced pressure. The oily residue was separated by fractional distillation. The desired product (3.4 g, 95% pure, yield 66%) was isolated at a transition temperature of 95° C. at 3.8 mbar.

$^1$H-NMR (CDCl$_3$): δ=3.9 (s; 3H), 6.75 (s; 1H), 7.4 ppm (s, 1H); $^{13}$C-NMR (CDCl$_3$): δ=39.9, 63.1, 95.1, 132.0, 147.8 ppm.

14. Preparation of 4-bromo-3-dichloromethyl-1-methylpyrazole

14.1 Preparation of (Z)-1,1-dichloro-3,4-dibromobut-3-en-2-one from 1,2-dibromoethylene and dichloroacetyl chloride At room temperature, dichloroacetyl chloride (5.4 g, 0.036 mol) was added dropwise (slightly exothermic) to a suspension of 1,2-dibromoethylene (10.2 g, 0.055 mol) and AlCl$_3$ (4.88 g, 0.036 mol). The reaction mixture was heated gradually to 55° C. and then worked up. The reaction mixture was added to ice-water (50 g) (the mixture foams and reacts violently) and was extracted three times with methylene chloride (100 ml). The organic phases were washed at 10° C. with saturated NaHCO$_3$ solution, dried over magnesium sulfate and filtered, and the solvent was removed under reduced pressure (30° C., 50 mbar). This gives 11.7 g of a black oil which comprises about 12% of (Z)-1,1-dichloro-3,4-dibromobut-3-en-2-one and 29% of (Z)-3-bromo-1,1,4-trichlorobut-3-en-2-one. The yield of (Z)-1,1-dichloro-3,4-dibromobut-3-en-2-one corresponds to 13%.

$^1$H-NMR (CDCl$_3$): δ=6.6 (s, 1H), 7.85 ppm (s, 1H); $^{13}$C-NMR (CDCl$_3$): δ=66.7, 129.6, 135.9, 179.6 ppm.

14.2 Preparation of 4-bromo-3-dichloromethyl-1-methylpyrazole from (Z)-1,1-dichloro-3,4-dibromobut-3-en-2-one At −40° C., a solution of (Z)-1,1-dichloro-3,4-dibromobut-3-en-2-one (50% pure, 10 g, 0.0685 mol) in diethyl ether (75 ml) was slowly added dropwise to an etherol solution of methylhydrazine (4 g, 0.086 mol). The mixture was subsequently stirred at 0° C. for 2 h and at room temperature overnight. The reaction mixture was then filtered, and the filter residue was washed with methyl tert-butyl ether (MTBE). Under reduced pressure, the solvent was removed from the filtrate. This gives 6.7 g of a brown oil having a 4-bromo-3-dichloromethyl-1-methylpyrazole content of 53% (according to GC analysis). This corresponds to a yield of 86.4%.

15. Preparation of 4-Bromo-3-difluoromethyl-1-methylpyrazole by fluorination of 4-bromo-1-methylpyrazole-3-carbaldehyde At −20° C., (diethylamino)sulfur trifluoride (DAST, 47.1 g, 0.29 mol) was added dropwise to a solution of 4-bromo-1-methylpyrazole-3-carbaldehyde (22.1 g, 0.12 mol) in methylene chloride (120 ml). The reaction mixture was stirred at room temperature overnight. The reaction mixture was then carefully added to an ice/water mixture (400 g) and extracted twice with methylene chloride (100 ml). The organic phase was washed twice with water (100 ml) and twice with a saturated aqueous NaCl solution (100 ml), dried over magnesium sulfate and filtered, and the solvent was removed under reduced pressure. The residue was separated by fractional distillation. 4-Bromo-3-difluoromethyl-1-methylpyrazole (transition temperature 51° C. at 2.5 mbar) was isolated in a purity of 97% (GC analysis) with a yield of 24.2 g (48.7%).

$^1$H-NMR (CDCl$_3$): δ=3.9 (s; 3H), 6.65 (t; 1H), 7.45 ppm (s, 1H).

16. Preparation of 4-bromo-3-difluoromethyl-1-methylpyrazole by halogen exchange At 160° C., 4-bromo-3-dichloromethyl-1-methylpyrazole (3.0 g; 0.01 mol; 90% pure according to GC analysis) was stirred with triethylamine trishydrofluoride (25 g, 0.16 mol) under autogenous pressure (<1 bar) for 1 h. After venting, the reaction mixture is added to ice (200 g), made alkaline with aqueous sodium hydroxide solution and extracted three times with methyl tert-butyl ether (100 ml). The combined organic phases were washed successively with dilute hydrochloric acid (100 ml) and a saturated aqueous NaCl solution (100 ml) and dried over magnesium sulfate, and the solvent was removed under reduced pressure. 4-Bromo-3-difluoromethyl-1-methylpyrazole was isolated in a purity of 81.3% (GC analysis) with a yield of 2.0 g (70%).

$^1$H-NMR (DMSO-d$_6$): δ=3.85 (s, 3H), 6.95 (t, 1H), 8.1 ppm (s, 1H).

17. Preparation of 3-difluoromethyl-1-methylpyrazole from 1-methylpyrazole-3-carbaldehyde At −20° C., (diethylamino)sulfur trifluoride (DAST, 87.8 g, 0.54 mol) was added dropwise to a solution of 1-methylpyrazole-3-carbaldehyde (20 g, 0.18 mol) in methylene chloride (200 ml). The reaction mixture was stirred at room temperature overnight. The reaction mixture was then added carefully to ice/water (400 g) and extracted twice with methylene chloride (100 ml each). The combined organic phase was washed twice with water (100 ml each) and twice with NaCl solution (100 ml each) and dried over magnesium sulfate, and the solvent was removed under reduced pressure. The residue was separated by fractional distillation. 3-Difluoromethyl-1-methylpyrazole (16.5 g, transition temperature 141° C. at 570 mbar) was isolated in a purity of 95%. This corresponds to a yield of 66.8%.

18. Preparation of 3-difluoromethyl-NH-pyrazole from propargylaldehyde dimethyl acetal

18.1 Preparation of 1,1-difluoro-4,4-dimethoxybut-2-yne

At −70° C., an n-buthyllithium solution (2.5 M, in hexane, 260 ml, 0.65 mol) was added dropwise to a solution of propargylaldehyde dimethyl acetal (52.8 g, 0.5 mol) in dried tetrahydrofuran (THF, 1000 ml). The reaction mixture was then stirred at −70° C. for 30 min and cooled to −100° C. At this temperature, chlorodifluoromethane (216.6 g, 2.5 mol) was introduced into the reaction mixture (strongly exothermic). The reaction mixture was slowly warmed to −50° C. and stirred at this temperature for 1 h. Aqueous saturated NH$_4$Cl solution (400 ml) was then added, the reaction mixture was warmed to 0° C., a water/MTBE mixture (500 ml) was added and the aqueous phase was removed. The aqueous phase was extracted twice with MTBE (200 ml). The combined organic phases were washed twice with dilute hydrochloric acid (100 ml), dried over magnesium sulfate and filtered, and the solvent was removed under reduced pressure. The residue was separated by fractional distillation. 1,1-Difluoro-4,4-dimethoxybut-2-yne (46.7 g; transition temperature 50-52° C. at 30 mbar) was obtained in a purity of 96% (according to GC analysis). This corresponds to a yield of 65%. More product was found in the cold trap and in the solvent that had been distilled off. Accordingly, the nonisolated yield is 71%.

$^1$H-NMR (CDCl$_3$): δ=3.4 (s, 6H), 5.2 (s, 1H), 6.25 ppm (t, 1H);
$^{13}$C-NMR (CDCl$_3$): δ=14.9, 61.4, 75.9, 83.9, 90.7, 103.4 ppm.

18.2 Preparation of 3-difluoromethyl-NH-pyrazole from 1,1-difluoro-4,4-dimethoxybut-2-yne At 55° C., a suspension of 1,1-difluoro-4,4-dimethoxybut-2-yne (98% pure, 0.3 g, 0.002 mol) and hydrazine sulfate (0.2 g, 0.0012 mol) in 2.5 ml of glacial acetic acid was stirred for 2 h. The reaction mixture was warmed to room temperature, a mixture of ethyl acetate and water (10 ml) was added and the reaction mixture was neutralized using dilute aqueous sodium hydroxide solution. After phase separation, the organic phase was washed twice with water (100 ml) and once with dilute aqueous NaCl solution, dried over magnesium sulfate and filtered, and the solvent was removed under reduced pressure. The red oily residue consisted to 70% of 3-difluoromethyl-NH-pyrazole (according to GC and $^1$H-NMR analysis). The yield corresponds to 75%.

$^1$H-NMR (CDCl$_3$): δ=6.65 (s, 1H), 6.8 (t, 1H), 7.68 (s, 1H), 10.2 ppm (s, 1H).

19. Preparation of 3-difluoromethyl-1-methylpyrazole from 1,1-difluoro-4,4-dimethoxy-but-2-yne A suspension of 1,1-difluoro-4,4-dimethoxybut-2-yne (98% pure, 1 g, 6.5 mmol), aqueous methylhydrazine (25% strength, 1.7 g, 13.0 mmol) and conc. sulfuric acid (0.7 g, 6.5 mmol) in glacial acetic acid (10 ml) was stirred at 100° C. for 6 h. The reaction mixture was warmed to room temperature, an ethyl acetate/water mixture (10 ml) was added and the reaction mixture was neutralized using dilute aqueous sodium hydroxide solution. After phase separation, the aqueous phase was extracted three times with ethyl acetate. The combined organic phases were washed twice with water (100 ml) and once with dilute aqueous NaCl solution and dried over magnesium sulfate, and the solvent was removed under reduced pressure. The red oily residue consisted to 61.8% of 3- and 5-difluoromethyl-1-methylpyrazole (according to GC and $^1$H-NMR analysis). The total yield of both isomers was 60.5%. The yield of 3-difluoromethyl-1-methylpyrazole was 29.2%.

20. Preparation of 1,1-difluoro-4,4-diethoxybut-2-yne

Analogously to the preparation of 1,1-difluoro-4,4-dimethoxybut-2-yne in example 17.1, 1,1-difluoro-4,4-diethoxybut-2-yne was prepared from diethyl acetal. The yield was 66.2%.

$^1$H-NMR (CDCl$_3$): δ=1.25 (t, 6H), 3.7 (m, 4H), 5.3 (s, 1H), 6.25 ppm (t, 1H).
$^{13}$C-NMR (CDCl$_3$): δ=52.9, 76.5, 83.2, 92.6, 103.5 ppm.

21. Preparation of 4-chloro-3-difluoromethyl-1-methylpyrazole

21.1 Preparation of (Z)-1,1,3,4-tetrachlorobut-3-en-2-one

At room temperature, dichloroacetyl chloride (50 g, 0.339 mol) was added dropwise (slightly exothermic) to a suspension of AlCl$_3$ (45 g, 0.339 mol) in 1,2-dichloroethylene (49.3 g, 0.508 mol). The reaction mixture was stirred under reflux conditions for 3 h and then at room temperature overnight. The reaction mixture was then stirred into ice water (500 g) (foams and reacts violently) and extracted three times with methylene chloride (200 ml). The combined organic phases were washed once at 10° C. with a saturated aqueous NaHCO$_3$ solution and dried over magnesium sulfate, and the solvent was removed at a bath temperature of 70° C. at atmospheric pressure. The residue was subjected to incipient distillation at 50 mbar and 70° C. This gives 46.5 g of a black oil having a (Z)-1,1,3,4-tetrachlorobut-3-en-2-one content of about 70% and contains 25% of a byproduct, which is (Z)-1,1,1,4-tetrachlorobut-3-en-2-one. Accordingly, the yield of (Z)-1,1,3,4-tetrachlorobut-3-en-2-one is 38%.

(Z)-1,1,3,4-Tetrachlorobut-3-en-2-one
$^1$H-NMR (CDCl$_3$): δ=6.6 (s, 1H), 7.85 ppm (s, 1H).
$^{13}$C-NMR (CDCl$_3$): δ=66.7, 129.6, 135.9, 179.6 ppm.

(Z)-1,1,1,4-Tetrachlorobut-3-en-2-one
$^1$H-NMR (CDCl$_3$): δ=7.15 (s; 1H), 7.7 ppm (s, 1H).
$^{13}$C-NMR (CDCl$_3$): δ=95.2, 123.2, 143.2, 177.5 ppm.

21.2 Preparation of 4-chloro-3-dichloromethyl-1-methylpyrazole

At −40° C., a solution of) (Z)-1,1,3,4-tetrachlorobut-3-en-2-one (60% strength, 10 g, 28.8 mmol) in diethyl ether (75 ml) was slowly added dropwise to an ethereal solution of methylhydrazine (4 g, 86 mmol). The reaction mixture was then stirred at 0° C. for 2 h and at room temperature overnight. The reaction mixture was filtered, and the filter cake was washed with methyl tert-butyl ether (MTBE). Under reduced pressure, the filtrate was freed from volatile components. The brown oil (10 g) obtained as a residue had, according to GC analysis, a 4-chloro-3-dichloromethyl-1-methylpyrazole content of 70%. The residue was subjected to a fractional distillation under reduced pressure (3.5 mbar). Distillation at 90-100° C. (bath: 157-190° C.) gave two fractions comprising 4-chloro-3-dichloromethyl-1-methylpyrazole (yield 70% of theory). As a further component, these fractions contained 1-methyl-3-trichloromethylpyrazole.

4-Chloro-3-dichloromethyl-1-methylpyrazole
$^1$H-NMR (CDCl$_3$): δ=3.9 (s, 3H), 6.75 (s, 1H), 7.35 ppm (s, 1H).
$^{13}$C-NMR (CDCl$_3$): δ=39.9, 146.3, 107.9, 129.7, 62.4 ppm.

1-Methyl-3-trichloromethylpyrazole
$^1$H-NMR (CDCl$_3$): δ=3.95 (s, 3H), 6.6 (s, 1H), 7.35 ppm (s, 1H).
$^{13}$C-NMR (CDCl$_3$): δ=39.5, 154.8, 104.4, 131.5, 90.7 ppm (CCl$_3$).

21.3 Preparation of 4-chloro-3-difluoromethyl-1-methylpyrazole

At 160° C., 4-chloro-3-dichloromethyl-1-methylpyrazole (2.2 g, 0.01 mol) was stirred with triethylamine trishydrofluoride (25 g, 0.16 mol) under autogenous pressure (<1 bar) for 1 h. After venting, the reaction mixture is added to ice (100 g), made alkaline with an aqueous NaOH solution and extracted three times with methyl tert-butyl ether (100 ml). The combined organic phases were washed successively with dilute hydrochloric acid (100 ml) and an aqueous NaCl solution (100 ml), dried over magnesium sulfate and filtered, and the solvent was removed under reduced pressure. The residue obtained was 4-chloro-3-difluoromethyl-1-methylpyrazole (1.5 g) which, according to GC analysis, had a purity of 99%. This corresponds to a yield of 4-chloro-3-difluoromethyl-1-methylpyrazole of 89%.

$^1$H-NMR (DMSO-d$_6$): δ=3.85 (s, 3H), 7.0 (t, 1H), 8.1 ppm (s, 1H).

22. Preparation of 3-difluoromethyl-NH-pyrazole from 3-dichloromethyl-NH-pyrazole Analogously to the preparation of 4-bromo-3-difluoromethyl-1-methylpyrazole by halogen exchange (example 15), 3-dichloromethyl-NH-pyrazole (1.4 g, 0.01 mol; 75% pure according to GC) was stirred at 80° C. with triethylamine trishydrofluoride (50 g, 0.31 mol) under autogenous pressure (<1 bar) for 13 h. After venting, the reaction mixture was added to ice (200 g), made alkaline with aqueous sodium hydroxide solution and extracted three times with methyl tert-butyl ether (MTBE, 100 ml). The combined organic phases were washed successively with dilute hydrochloric acid (100 ml) and a saturated aqueous NaCl solution (100 ml), dried over magnesium sulfate and filtered, and the solvent was removed under reduced pressure. 4-Bromo-3-difluoromethyl-1-methylpyrazole was isolated in a purity of 87% (GC analysis) with a yield of 0.7 g (44%).

$^1$H-NMR (DMSO-d$_6$): δ=3.85 (s, 3H), 6.95 (t, 1H), 8.1 ppm (s, 1H).

23. Preparation of N-(2-(2-cyclopropylcyclopropyl)phenyl)-3-difluoromethyl-1-methylpyrazole-4-carboxamide in the presence of 2,2-dimethyl-1,3-bis(diphenyl-phosphino)propane (Pepstar)

A solution of Pd(PhCN)$_2$Cl$_2$ (0.014 mmol) and Pepstar (0.042 mmol) in dimethyl-formamide (DMF, 3 ml) was stirred at room temperature for 30 minutes. The solution comprising the pre-formed catalyst was transferred into an inertized autoclave. In a CO countercurrent, diazabicycloundecene (DBU, 3.08 mmol) and solutions of 3-difluoro-methyl-1-methyl-4-bromopyrazole (2.8 mmol) and 2-(2-cyclopropylcyclopropyl)aniline (2.8 mmol) in DMF (3.25 ml each) were added to the solution of the catalyst in the autoclave. The reaction mixture was shaken at room temperature for 10 min and at 150° C. and a CO pressure of 15 bar for a further 16 h.

The conversion based on bromopyrazole was 97.6% at a selectivity of 83.4%. The composition of the reaction discharge was, according to GC analysis, as follows: DMF 33.51 area %, bromopyrazole 0.83 area %, DBU 31.65 area %, 2-(2-cyclopropylcyclo-propyl)aniline 0.0 area %, N-(2-(2-cyclopropylcyclopropyl)phenyl)-3-difluoromethyl-1-methylpyrazole-4-carboxamide 28.37 area %.

Work-up was carried out as described in example 2.i), giving an isolated yield of N-(2-cyclopropylcyclopropyl)phenyl)-3-difluoromethyl-1-methylpyrazole-4-carboxamide of 81.4%

24. Preparation of N-(2-(3,4-dichlorophenyl)-4-fluorophenyl)-3-difluoromethyl-1-methylpyrazole-4-carboxamide in the presence of 2,2-dimethyl-1,3-bis(diphenyl-phosphino)propane (Pepstar)

A solution of Pd(PhCN)$_2$Cl$_2$ (0.014 mmol) and Pepstar (0.042 mmol) in dimethyl-formamide (DMF, 3 ml) was stirred at room temperature for 30 minutes. The solution comprising the pre-formed catalyst was transferred into an inertized autoclave. In a CO countercurrent, diazabicycloundecene (DBU, 3.08 mmol) and solutions of 3-difluoro-methyl-1-methyl-4-bromopyrazole (2.8 mmol) and 2-(3,4-dichlorophenyl)-4-fluoroaniline (2.8 mmol) in DMF (3.25 ml each) were added to the solution of the catalyst in the autoclave. The reaction mixture was shaken at room temperature for 10 min and at 150° C. and a CO pressure of 15 bar for a further 16 h.

The conversion based on 4-bromopyrazole was 97.2% at a selectivity of 56.8%. The composition of the reaction discharge was, according to GC analysis, as follows: DMF 32.65 area %, bromopyrazole 1.50 area %, DBU 14.64 area %, 2-(3,4-dichlorophenyl)-4-fluoroaniline 3.29 area %, N-(2-(3,4-dichlorophenyl)-4-fluorophenyl)-3-difluoromethyl-1-methylpyrazole-4-carboxamide 29.11 area %.

Work-up was carried out as described in example 2.i), giving an isolated yield of N-(2-(3,4-dichlorophenyl-4-fluorophenyl)-3-difluoromethyl-1-methylpyrazole-4-carboxamide of 55.2%.

25. Preparation of N-(9-isopropylbenzonorbornen-5-yl)-3-difluoromethyl-1-methyl-pyrazole-4-carboxamide in the presence of 2,2-dimethyl-1,3-bis(diphenylphosphino)propane (Pepstar)

A solution of Pd(PhCN)$_2$Cl$_2$ (0.0375 mmol) and Pepstar (0.1125 mmol) in dimethyl-formamide (DMF, 10 ml) was stirred at room temperature for 30 minutes. The solution comprising the pre-formed catalyst was transferred into an inertized autoclave. In a CO countercurrent, diazabicyclodecene (DBU, 16.5 mmol) and solutions of 3-difluoro-methyl-1-methyl-4-bromopryazole (16.5 mmol) and 5-amino-9-isopropylbenzo-norbornene (15 mmol) in DMF (in each case 25 ml) were added to the solution of the catalyst in the autoclave. The reaction mixture was stirred at 150° C. and a CO pressure of 15 bar for 24 h.

The conversion based on the bromopyrazole was almost quantitative, at a selectivity of 38%. The composition of the reaction discharge was, according to GC analysis, as follows: DMF 73.8 area %, bromopyrazole 0.02 area %, DBU 8.2 area %, amino-isopropylbenzonorbornene 7.1 area % and N-(9-isopropylbenzonorbornen-5-yl)-3-difluoromethyl-1-methylpyrazole-4-carboxamide 4.08 area %.

Work-up was carried out as described in example 2.i), giving an isolated yield of N-(9-isopropylbenzonorbornen-5-yl)-3-difluoromethyl-1-methylpyrazole-4-carboxamide of 38%.

26. Preparation of 3-difluoromethyl-N-methylpyrazole by halogen exchange

3-Dichloromethyl-N-methylpyrazole (40.0 g; 0.21 mol; 84.8% pure according to GC analysis) comprising, as minor component, 5-dichloromethyl-N-methylpyrazole was stirred with triethylamine trishydrofluoride (199 g, 1.23 mol) at 160° C. under intrinsic pressure (<1 bar) for 1 h. The reaction mixture was vented and poured onto ice (500 g), made alkaline using aqueous sodium hydroxide solution and extracted three times with methyl tert-butyl ether (100 ml). The organic phases were combined, washed successively with hydrochloric acid (dilute, 100 ml) and a saturated aqueous NaCl solution (100 ml), dried over magnesium sulfate and freed from the solvent under reduced pressure. The residue obtained was 3-difluoromethyl-1-methylpyrazole (24.8 g, yield: 78%) in a purity of 85.4% (according to GC analysis) comprising, as minor component, 5-difluoromethyl-N-methylpyrazole.

27. Selective bromination of 3-difluoromethyl-N-methylpyrazole over 5-difluoro-methyl-N-methylpyrazole At a temperature of 25° C., bromine (3.2 g, about 1 eq.) is added dropwise to a solution of an isomer mixture of 3-difluoromethyl-N-methylpyrazole and 5-difluoromethyl-N-methylpyrazole (2.8 g; ratio according to GC analysis: 10:1) in methylene chloride (20 ml). The reaction mixture is stirred at 25° C. for a total of 5 h. According to GC analysis, 67% of the 3-difluoromethyl-N-methylpyrazole had been converted, whereas most of the 5-difluoromethyl-N-methylpyrazole was present in unreacted form in the reaction mixture. After further addition of bromine (1.6 g, about 0.5 eq.), the reaction mixture was stirred at 25° C. for a further 22 h. According to GC analysis, 96% of the 3-difluoromethyl-N-methylpyrazole had been converted, whereas most of the 5-difluoromethyl-N-methylpyrazole was present in unreacted form in the reaction mixture. The reaction mixture was diluted with methylene chloride (20 ml) and washed with an aqueous solution of sodium thiosulfate (0.1 M, 70 ml). The organic phase thus obtained contained, in addition to 4-bromo-3-difluoromethyl-N-methylpyrazole, the unreacted 5-difluoromethyl-N-methylpyrazole. The 4-bromo-3-difluoromethyl-N-methylpyrazole was isolated in high purity by fractional distillation.

28. Selective bromination of 3-difluoromethyl-N-methylpyrazole using NBS

At from 3 to 5° C., a solution of N-bromosuccinimide (NBS, 54 g, 0.3 mol) in dimethyl-formamide (DMF, 100 ml) was added dropwise to a solution of 3-difluoromethyl-N-methylpyrazole (49.3 g, 0.3 mol; 81.4% pure according to GC analysis) comprising, as minor component, 5.2% of 5-difluoromethyl-N-methylpyrazole, based on the total amount of the isomer mixture, in DMF (100 ml). The reaction mixture was then warmed to room temperature and stirred for a further 12 h. With stirring, the reaction mixture was then poured into water (1000 ml) and extracted twice with methyl tert-butyl ether (MTBE, 300 ml). The organic phases were combined, washed with a saturated aqueous solution of NaCl, dried over magnesium sulfate, filtered and then freed from the solvent under reduced pressure. 4-Bromo-3-difluoromethyl-N-methylpyrazole was obtained as an oil (76.6 g; purity: 74.2% according to GC analysis) comprising 4.5% of unreacted 5-difluoromethyl-N-methylpyrazole. This corresponds to a yield of 89%.

29. Selective chlorination of 3-difluoromethyl-N-methylpyrazole using NCS

At 0-5° C., a solution of N-chlorosuccinimide (NCS, 12.6 g, 0.09 mol) in dimethyl-formamide (DMF, 70 ml) was added dropwise to a solution of 3-difluoromethyl-N-methylpyrazole (14.9 g, 0.09 mol, 83.7% pure according to GC analysis) comprising, as minor component, 4.1% of 5-difluoromethyl-N-methylpyrazole, based on the total amount of the isomer mixture, in DMF (30 ml). The reaction mixture was then heated at 60° C. and stirred for a further 12 h. With stirring, the reaction mixture was then poured into water (1000 ml) and extracted twice with methyl tert-butyl ether (MTBE, 150 ml). The organic phases were combined, washed with a saturated aqueous solution of NaCl, dried over magnesium sulfate, filtered and then freed from the solvent under reduced pressure. 4-Chloro-3-difluoromethyl-N-methylpyrazole was obtained as an oil (17.6 g; purity: 78.4% according to GC analysis) comprising 3.7% of unreacted 5-difluoromethyl-N-methylpyrazole. This corresponds to a yield of 88%.

The invention claimed is:

1. A process for preparing compounds of the formula (I)

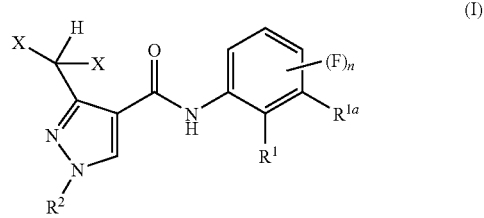

(I)

in which

R$^1$ is phenyl or C$_3$-C$_7$-cycloalkyl which are unsubstituted or have 1, 2 or 3 substituents R$^{a1}$ independently of one another selected from the group consisting of halogen, C$_1$-C$_8$-alkyl, C$_1$-C$_4$-alkoxy, C$_1$-C$_4$-alkylthio, C$_1$-C$_4$-haloalkyl, C$_1$-C$_4$-haloalkoxy, C$_1$-C$_4$-haloalkylthio and C$_3$-C$_7$-cycloalkyl, R$^{1a}$ is hydrogen or fluorine, or R$^{1a}$ together with R$^1$ is C$_3$-C$_5$-alkandiyl or C$_5$-C$_7$-cycloalkanediyl, where C$_3$-C$_5$-alkanediyl and C$_5$-C$_7$-cycloalkanediyl are unsubstituted or have 1, 2 or 3 substituents selected from the group consisting of C$_1$-C$_4$-alkyl radicals, R$^2$ is hydrogen, C$_1$-C$_6$-alkyl, C$_2$-C$_6$-alkenyl, C$_2$-C$_6$-alkynyl or C$_1$-C$_4$-alkoxy-C$_1$-C$_2$-alkyl, X is F or Cl and n is 0, 1, 2 or 3;

which comprises

A) providing a compound of the formula (II)

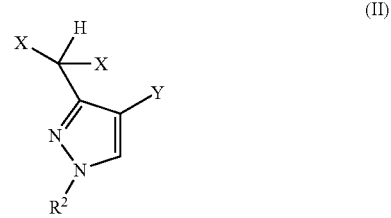

(II)

in which

X is F or Cl,

Y is Cl or Br and

R$^2$ has one of the meanings given above; and

B) reacting a compound of the formula (II) with carbon monoxide and a compound of the formula (III),

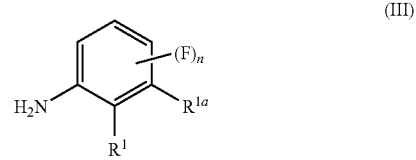

(III)

in which R$^1$, R$^{1a}$ and n have one of the meanings given above, in the presence of a palladium catalyst.

2. The process according to claim 1 in which the compound of the formula (I) is selected from among compounds of the formula (I.1)

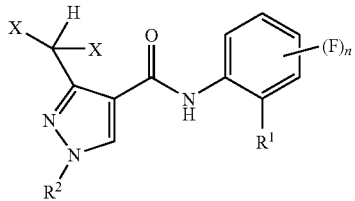
(I.1)

in which $R^1$, $R^2$, X and n independently of one another have one of the meanings given for the compounds of the formula (I),
and in which the compound of the formula (III) is selected from among compounds of the formula (III.1)

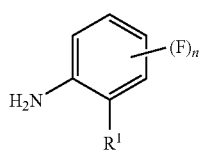
(III.1)

in which $R^1$ and n independently of one another have one of the meanings given for the compounds of the formula (III).

3. The process according to claim 1 in which the provision of a compound of the formula (II) in which Y represents Br or Cl comprises,
A.1) providing a compound of the formula (IV)

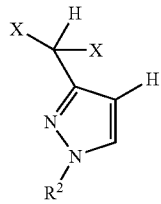
(IV)

in which
X represents chlorine or fluorine, and
A.2) in the case that X in the compound of the formula (IV) is chlorine, a halogen exchange for fluorine and
A.3) chlorinating or brominating the compound of the formula (IV).

4. The process according to claim 3 wherein a compound of the formula (IV) is provided in which X is chlorine, this compound is subjected to a halogen exchange for fluorine and the resulting compound of the formula (IV) in which X is fluorine is then chlorinated or brominated.

5. The process according to claim 4 wherein the halogen exchange is carried out by reacting the compound of formula (IV) with a fluorinating agent selected from the group consisting of alkali metal fluorides, cobalt(III) fluoride, antimony fluoride, molybdenum fluoride, hydrogen fluoride, hydrogen fluoride/pyridine mixtures, tertiary ammonium hydrofluorides and trialkylamine hydrofluorides of the general formula n*HF/N($C_1$-$C_4$-alkyl)$_3$, wherein n is 1, 2 or 3.

6. The process according to claim 5 wherein the compound of the formula (IV) is subjected to the chlorination or bromination in the form of a mixture with the corresponding 5-isomer and the compound of the formula (II) thus obtained is then separated from the unreacted 5-isomer wherein the 5-isomer is of the formula

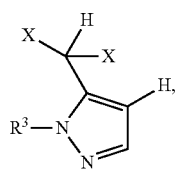
(iso-IV)

in which X is fluorine or chlorine.

7. The process according to claim 3 in which the provision of a compound of the formula (IV) comprises
A.1.1a) providing a compound of the formula (V)

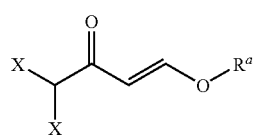
(V)

in which
X is Cl or fluorine and
$R^a$ is $C_1$-$C_6$-alkyl or $C_2$-$C_6$-alkenyl, and
A.1.2a) reacting the compound of the formula (V) with a hydrazine compound of the formula $R^2$HN—$NH_2$.

8. The process according to claim 3 in which the provision of a compound of the formula (IV) comprises
A.1.1b) providing a compound of the formula (VI)

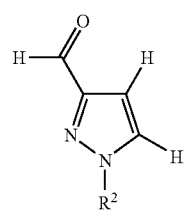
(VI)

and
A.1.2b) reacting the compound of the formula (VI) by converting the carbonyl group into a dihalomethyl group using a suitable halogenating agent.

9. The process according to claim 3 in which the provision of a compound of the formula (IV) comprises
A.1.1c) deprotonating a propargylaldehyde acetal,
A.1.2c) reacting the deprotonated propargylaldehyde acetal from step A.1.1c) with a compound of the formula $CHX_2Cl$ in which X is F or Cl, and
A.1.3c) subsequently converting the reaction product from step A.1.2c) into a compound of the formula (IV) using a hydrazine compound of the formula $R^2$HN—$NH_2$.

10. The process according to claim 3 in which the provision of a compound of the formula (IV) in which X is fluorine comprises A.1.1d) providing a compound of the formula (VII)

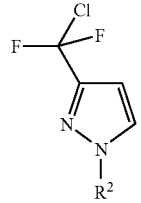
(VII)

and

A.1.2d) dechlorinating the compound of the formula (VII).

11. The process according to claim 3 in which the provision of a compound of the formula (IV) comprises A.1.1e) providing a compound of the formula (VIII)

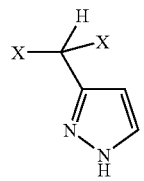
(VIII)

in which X is Cl or fluorine and

A.1.2e) N-alkylating the compound of the formula (VIII).

12. The process according to claim 11 wherein, to provide a compound of the formula (VIII), a compound of the formula V

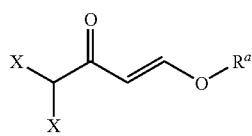
(V)

in which
X is Cl or fluorine and
$R^a$ is $C_1$-$C_6$-alkyl or $C_2$-$C_6$-alkenyl
is reacted with hydrazine.

13. The process according to claim 11 wherein, to provide a compound of the formula (VIII), an acetal of propargylaldehyde is deprotonated,
the resulting deprotonated acetal of the propargylaldehyde is reacted with a compound of the formula $CHX_2Cl$ in which X is F or Cl,
and the resulting reaction product is subjected to a reaction with hydrazine.

14. The process according to claim 11 in which the provision of a compound of the formula (VIII) in which X is F comprises
providing a compound of the formula (IX)

(IX)

and dechlorinating the compound of the formula (IX).

15. The process according to claim 1 in which the provision of a compound of the formula (II) comprises A.1') providing a compound of the formula (VI)

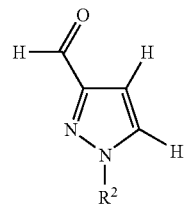
(VI)

in which $R^2$ has one of the meanings given above; and

A.2') chlorinating or brominating the compound of the formula (VI) in the 4-position of the pyrazole, giving a compound of the formula (X)

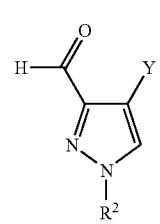
(X)

in which Y is Cl or Br, and

A.3') converting the carbonyl group of the compound of the formula (X) into a dihalomethyl group.

16. The process according to claim 1 in which the provision of a compound of the formula (II) in which Y is Cl comprises
A.1") providing a compound of the formula (XI)

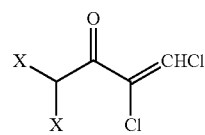
(XI)

in which X is F or chlorine,

A.2") reacting the compound of the formula (XI) with a suitable hydrazine derivative of the formula $R^2HN—NH_2$ to give a compound of the general formula (II) in which X is F or Cl, and Y is Cl, and A.3") in the case that X in the compound of the formula (II) is chlorine, a halogen exchange for fluorine.

17. The process according to claim 1 in which X in the compounds of the general formula (I) is fluorine.

18. A compound of the general formula (II)

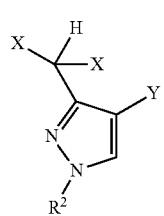
(II)

in which

X is F or Cl,

Y is Cl or Br and $R^2$ is hydrogen, $C_1$-$C_6$-alkyl, $C_2$-$C_6$-alkenyl, $C_2$-$C_6$-alkynyl or $C_1$-$C_4$-alkoxy-$C_1$-$C_2$-alkyl.

19. The compound according to claim 18 in which Y is chlorine.

20. The compound according to claim 18 in which Y is bromine.

21. The compound according to claim 18 in which X is fluorine.

22. The compound according to claim 18 in which X is chlorine.

23. A compound of the general formula (IV)

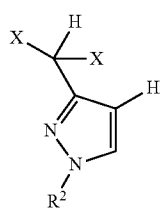

(IV)

in which

X represents fluorine and $R^2$ is hydrogen, $C_1$-$C_6$-alkyl, $C_2$-$C_6$-alkenyl, $C_2$-$C_6$-alkynyl or $C_1$-$C_4$-alkoxy-$C_1$-$C_2$-alkyl.

24. A compound of the general formula (IV)

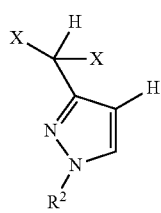

(IV)

in which X is chlorine and $R^2$ is $C_1$-$C_6$-alkyl, $C_2$-$C_6$-alkenyl, $C_2$-$C_6$-alkynyl or $C_1$-$C_4$-alkoxy-$C_1$-$C_2$-alkyl.

25. A compound of the general formula (VII)

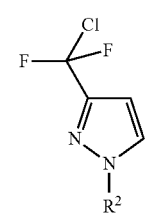

(VII)

in which $R^2$ is hydrogen, $C_1$-$C_6$-alkyl, $C_2$-$C_6$-alkenyl, $C_2$-$C_6$-alkynyl or $C_1$-$C_4$-alkoxy-$C_1$-$C_2$-alkyl.

26. A compound of the general formula (VIII)

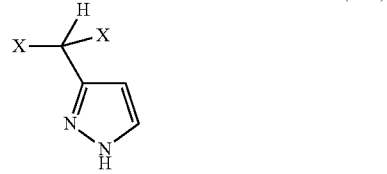

(VIII)

in which X is fluorine.

27. A process for preparing compounds of the formula (II) as defined in claim 18 which comprises A.1) providing a compound of the formula (IV)

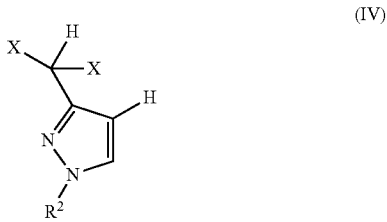

(IV)

in which

X is chlorine or fluorine and $R^2$ has one of the meanings given in claim 18,

A.2) in the case that X in the compound of the formula (IV) is chlorine, a halogen exchange for fluorine and A.3) chlorinating or brominating a compound of the formula (IV).

28. The process according to claim 27 wherein a compound of the formula (IV) is provided in which X is chlorine, this compound is subjected to a halogen exchange for fluorine and the resulting compound of the formula (IV) in which X is fluorine is then chlorinated or brominated.

29. The process according to claim 28 wherein the halogen exchange is carried out by reacting the compound of formula (IV) with a fluorinating agent selected from the group consisting of alkali metal fluorides, cobalt(III) fluoride, antimony fluoride, molybdenum fluoride, hydrogen fluoride, hydrogen fluoride/pyridine mixtures, tertiary ammonium hydrofluorides and trialkylamine hydrofluorides of the general formula n*HF/N($C_1$-$C_4$-alkyl)$_3$, where n is 1, 2 or 3.

* * * * *